(12) United States Patent
Weiss et al.

(10) Patent No.: US 10,150,083 B2
(45) Date of Patent: Dec. 11, 2018

(54) SEPARATION OF MIXED XYLENES

(71) Applicant: ExxonMobil Research and Engineering Company, Annandale, NJ (US)

(72) Inventors: Brian Weiss, Bridgewater, NJ (US); Benjamin A. McCool, Annandale, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 177 days.

(21) Appl. No.: 15/348,010

(22) Filed: Nov. 10, 2016

(65) Prior Publication Data

US 2017/0137350 A1    May 18, 2017

Related U.S. Application Data

(60) Provisional application No. 62/367,175, filed on Jul. 27, 2016, provisional application No. 62/367,168, (Continued)

(51) Int. Cl.
*B01D 71/02* (2006.01)
*C07C 15/08* (2006.01)
(Continued)

(52) U.S. Cl.
CPC ......... *B01D 61/025* (2013.01); *B01D 53/228* (2013.01); *B01D 61/002* (2013.01); *B01D 61/007* (2013.01); *B01D 67/0067* (2013.01); *B01D 69/08* (2013.01); *B01D 69/12* (2013.01); *B01D 69/125* (2013.01); *B01D 71/021* (2013.01); *B01D 71/022* (2013.01); *C02F 1/441* (2013.01); *C07C 5/2732* (2013.01); *C07C 7/005* (2013.01); *C07C 7/14* (2013.01);
(Continued)

(58) Field of Classification Search
None
See application file for complete search history.

(56) References Cited

U.S. PATENT DOCUMENTS 4,510,047 A    4/1985  Thompson
4,571,444 A    2/1986  Black et al.
(Continued)

FOREIGN PATENT DOCUMENTS

EP    0428052 A2    11/1990
JP    2013094744 A2    5/2013

OTHER PUBLICATIONS

International Search Report and Written Opinion PCT/US2016/061263 dated Mar. 9, 2017.
(Continued)

*Primary Examiner* — Jennifer A Leung
(74) *Attorney, Agent, or Firm* — Andrew T. Ward; Priya G. Prasad

(57) ABSTRACT

Asymmetric membrane structures are provided that are suitable for hydrocarbon reverse osmosis of small hydrocarbons. Separation of para-xylene from ortho- and meta-xylene is an example of a separation that can be performed using hydrocarbon reverse osmosis. Hydrocarbon reverse osmosis separations can be incorporated into a para-xylene isomerization and recovery system in a variety of manners.

10 Claims, 22 Drawing Sheets

Related U.S. Application Data filed on Jul. 27, 2016, provisional application No. 62/254,792, filed on Nov. 13, 2015.

(51) Int. Cl.

| | | |
|---|---|---|
| C07C 7/144 | (2006.01) | |
| C07C 5/27 | (2006.01) | |
| B01D 61/02 | (2006.01) | |
| B01D 67/00 | (2006.01) | |
| B01D 69/08 | (2006.01) | |
| B01D 69/12 | (2006.01) | |
| C07C 7/14 | (2006.01) | |
| B01D 53/22 | (2006.01) | |
| B01D 61/00 | (2006.01) | |
| C02F 1/44 | (2006.01) | |
| C07C 7/00 | (2006.01) | |
| C02F 103/08 | (2006.01) | |

(52) U.S. Cl.
CPC .............. C07C 7/144 (2013.01); C07C 15/08 (2013.01); B01D 2323/30 (2013.01); B01D 2325/022 (2013.01); B01D 2325/04 (2013.01); C02F 2103/08 (2013.01)

(56) References Cited

U.S. PATENT DOCUMENTS

| 4,685,940 | A | 8/1987 | Soffer et al. |
|---|---|---|---|
| 5,470,482 | A | 11/1995 | Holt |
| 5,750,820 | A | 5/1998 | Wei |
| 5,972,079 | A * | 10/1999 | Foley ................... B01D 71/021 55/524 |
| 6,376,733 | B1 * | 4/2002 | Ferraro ................... C07C 7/005 585/321 |
| 8,529,757 | B2 | 9/2013 | Go et al. |
| 8,697,929 | B2 | 4/2014 | Ou et al. |
| 2005/0045029 | A1 * | 3/2005 | Colling ................ B01D 53/225 95/46 |
| 2008/0071126 | A1 | 3/2008 | Ou et al. |
| 2009/0149686 | A1 * | 6/2009 | Leflaive ................. C07C 7/005 585/478 |
| 2011/0155662 | A1 | 6/2011 | Liu et al. |
| 2014/0100406 | A1 | 4/2014 | Liu et al. |
| 2015/0321147 | A1 | 11/2015 | Fleming et al. |

OTHER PUBLICATIONS

Koros et al., "Water and Beyond: Expanding the Spectrum of Large-Scale Energy Efficient Separation Processes", AIChE Journal, Jul. 31, 2012, pp. 2624-2633, vol. 58, iss. 9, John Wiley & Sons, Inc.

Xu et al., "Olefins-selective asymmetric carbon molecular sieve hollow fiber membranes for hybrid membrane-distillation processes for olefin/paraffin separations", Journal of Membrane Science, 2012, pp. 314-323. vol. 423-424, iss. 15, Elsevier, ScienceDirect.

Minceva et al., "Modeling and simulation of a simulated moving bed for the separation of p-ylene", Industrial and Engineering Chemistry Research, 2002, pp. 3454-3461, vol. 416. iss. 14, ACS Publications.

Kiyono et al., "Effect of pyrolysis atmosphere on separation performance of carbon molecular sieve membranes", Journal of Membrane Science, 2010, pp. 2-10, vol. 359, iss. 1, Elsevier, ScienceDirect.

Kiyono et al., "Effect of polymer precursors on carbon molecular sieve structure and separation performance properties", Carbon, 2010, pp. 4432-1141, vol. 48, iss. 15, Elsevier, ScienceDirect.

Kiyono et al., "Generalization of effect of oxygen exposure on formation and performance of carbon molecular sieve membranes", Carbon, 2010, pp. 4442-4449, vol. 48 iss. 15, Elsevier, ScienceDirect.

Williams et al., "Gas separation by carbon membranes", Advanced Membrane Technology and Applications, 2010, pp. 599-631, John Wiley & Sons, Inc.

Vu et al.,, "Effect of condensable impurity in CO2/CH4 gas feeds on performance of mixed matrix membranes using carbon molecular sieves", Journal of membrane science, 2003, pp. 233-239, vol. 221, iss. 1, Elsevier, ScienceDirect.

Rungta et al., "Carbon molecular sieve dense film membranes derived from Matrimid® for ethylene/ethane separation", Carbon, 2012, pp. 1488-1502, vol. 50, iss. 4, Elsevier, ScienceDirect.

Ma et al., "Carbon molecular sieve gas separation membranes based on an intrinsically microporous polyimide precursor", Carbon, 2013, pp. 88-96, vol. 62, Elsevier, ScienceDirect.

Xu et al., "Matrimid® derived carbon molecular sieve hollow fiber membranes for ethylene/ethane separation", Journal of Membrane Science, 2011, pp. 138-147, vol. 380, iss. 1, Elsevier, ScienceDirect.

Cussler, "On separation efficiency", AIChE Journal, 2012, pp. 3825-3831, vol. 58, iss. 12, John Wiley & Sons, Inc.

Wade, "Distillation plant development and cost update", Desalination. 2001, pp. 3-12, vol. 136, iss. Elsevier, ScienceDirect.

Avlontis et al., "Energy consumption and membrane replacement cost for seawater RO desalination plants", Desalination, 2003, pp. 151-158, vol. 157, iss 1-3, Elsevier, ScienceDirect.

White, "Development of large-scale applications in organic solvent nanofiltration arid pervaporation for chemical and refining processes", Journal of membrane science, 2006, pp. 26-35, vol. 286, iss, 1, Elsevier, ScienceDirect.

Bhore et al., "New membrane process debottlenecks solvent dewaxing unit", Oil and Gas Journal, 1999, pp. 67-74, vol. 97, iss. 46, Pettroleum Pub. Co.

Gould et al., "Membrane separation in solvent lube dewaxing", Environmental Progress, 2001, pp. 12-16, vol. 20, iss. 1, John Wiley & Sons, Inc.

Silva et al. "Solvent transport in organic solvent nanofiltration membranes",Journal of membrane science, 2005, pp. 4-59, vol. 262, iss, 1, Elsevier, ScienceDirect.

Lin et al., "Nanofiltration membrane cascade for continuous solvent exchange", Chemical Engineering Science, 2007, pp. 2728-2736, vol. 62, iss. 10, Elsevier, ScienceDirect.

Schmidt et al., "Characterisation of organic solvent nanofiltration membranes in multi-component mixtures: Phenomena-based modelling and membrane modelling maps", Journal of Membrane Science, 2013, pp. 183-199, vol. 445, iss. 15, Elsevier; ScienceDirect.

Whu et al., "Nanofiltration studies of larger organic rnicrosolutes in methanol solutions", Journal of Membrane Science, 2000, pp. 159-172, vol. 170, Elsevier, ScienceDirect.

Wijmans et al., "The solution-diffusion model: a review", Journal of membrane science, 1995, pp. 1-21, vol. 107, iss. 1, Elsevier, ScienceDirect.

See Toh et al., "Polymeric membranes for nanofiltration in polar aprotic solvents," Journal of Membrane Science, 2007, pp. 3-10, vol. 301, iss. 1, Elsevier, ScienceDirect.

Razdan et al., "Novel membrane processes for separation of organics", Current Science, 2003, pp. 761, vol. 85, iss. 6.

Gibbins et al., "Observations on solvent flux and solute rejection across solvent resistant nanofiltration membranes", Desalination, 2002, pp. 307-313, vol. 147, iss. 1, Elsevier, ScienceDirect.

See Toh et al., "The influence of membrane formation parameters on the functional performance of organic solvent nanofiltration membranes",Journal of membrane science, 2007, pp. 236-250, vol. 299, iss. 1, Elsevier, ScienceDirect.

Guizard et al., "Potentiality of organic solvents filtration with ceramic membranes. A comparison with polymer membranes", Desalination, 2002, pp. 275-280, vol. 147, iss. 1, Elsevier, ScienceDirect.

Kingsbury et al., "A morphological study of ceramic hollow fibre membranes", Journal of Membrane Science, 2009, pp. 134-140, vol. 328, iss. 1, Elsevier, ScienceDirect.

PCT/US2016/061251 International Search Report and Written Opinion dated Feb. 21, 2017.

Bhuwania et al., "Engineering substructure morphology of asymmetric carbon molecular siev hollow fiber membranes", Carbon; Sep. 1, 2014, pp. 417-434, vol. 76, Elsevier, ScienceDirect.

Koresh et al., "Molecular Siev Carbon Perrnselective Membrane. Part I. Presentation of a New Device for Gas Mixture Separation", Separation Science and Technology, Jun. 5, 1983, pp. 723-745, vol. 18, No. 8.

(56) References Cited

OTHER PUBLICATIONS

Koh, et al., "Reverse osmosis molecular differentiation of organic liquids using carbon molecular sieve membranes", Science, Aug. 19, 2016, pp. 804-807; vol. 353, No. 6301, American Association for the Advancement of Science.
PCT/US2016/061259 International Search Report and Written Opinion dated Feb. 23, 2017.

\* cited by examiner

SEPARATION OF MIXED XYLENES

CROSS-REFERENCE TO RELATED APPLICATIONS

This application claims priority to U.S. Provisional Application Ser. No. 62/367,175 and U.S. Provisional Application Ser. No. 62/367,168 both filed on Jul. 27, 2016, and U.S. Provisional Application Ser. No. 62/254,792 filed on Nov. 13, 2015 each of which are herein incorporated by reference in their entirety.

FIELD

This description is related to treatment and separation of mixed xylenes based in part on reverse osmosis membrane separation of various compounds.

BACKGROUND

Many petroleum refining and chemical production processes include one or more separation processes for isolating desirable products. Membrane separations are a potentially desirable method of separation due to the low energy requirements for performing a separation. However, use of membrane separations is limited to situations where a suitable membrane is available for performing a commercial scale separation.

Separation of para-xylene from other $C_8$ aromatics is an example of a separation that is difficult to perform via a boiling point separation. Current commercial methods involve selective crystallization or simulated moving bed chromatography to separate para-xylene from ortho- and meta-xylene. These methods are energy and/or equipment intensive.

U.S. Pat. No. 4,510,047 describes regenerated cellulose membranes for use in reverse osmosis separation of hydrocarbonaceous compounds, such aromatic extraction solvents. The regenerated cellulose membranes are susceptible to pore swelling in the presence of such solvents.

U.S. Pat. No. 4,571,444 describes methods for separating alkylaromatic compounds from aromatic solvents using asymmetric polyimide fiber membranes. The membrane is described as being suitable for at least partially separating benzene, toluene, and/or ethyl benzene from single ring aromatic compounds that are alkylated with a $C_8$ to $C_{20}$ alkyl group.

SUMMARY

In various aspects, systems and methods are provided for performing xylene isomerization and/or separation. For example, in an aspect a system for xylene isomerization and separation can include a separation stage based on boiling point separation configured to generate at least a para-xylene enriched fraction; a xylene recovery unit in fluid communication with the separation stage for receiving the para-xylene enriched fraction from the separation stage, the xylene recovery unit comprising a product outlet and a residual outlet; a membrane structure in fluid communication with the residual outlet for receiving at least a portion of residual stream; and a liquid phase isomerization reactor in fluid communication with the membrane structure for receiving a retentate from the membrane structure.

In another aspect, a system for xylene isomerization and separation can include a separation stage based on boiling point separation configured to generate at least a para-xylene enriched fraction; at least one membrane structure for forming a permeate comprising para-xylene and a retentate; and an isomerization reactor in fluid communication with the membrane structure for receiving the retentate from the membrane structure.

In yet another aspect, a method for xylene isomerization and separation, can include exposing a xylene-containing feed to an isomerization catalyst under liquid phase isomerization conditions to produce an isomerized effluent; and performing a membrane separation on at least a portion of the isomerized effluent to produce a permeate enriched in para-xylene relative to the xylene-containing feed and the isomerized effluent.

In some aspects, the membrane structure can correspond to a membrane structure comprising a plurality of membrane layers. A first membrane layer having a pore volume of at least 0.2 $cm^3/g$ of pores with a median pore size of at least 20 nm, a second membrane layer comprising a porous carbon layer having a BET surface area of at least about 100 $m^2/g$ (or at least about 300 $m^2/g$), the second membrane layer having a pore size distribution comprising a smallest substantial pore size peak having a median pore size of about 5.8 Angstroms to about 7.0 Angstroms. Optionally, the smallest substantial pore size peak can have a median pore size of about 5.8 Angstroms to about 6.8 Angstroms, or about 6.0 to about 6.5 Angstroms. Optionally, the membrane structure can correspond to a hollow fiber membrane structure.

DETAILED DESCRIPTION

Figure 1:
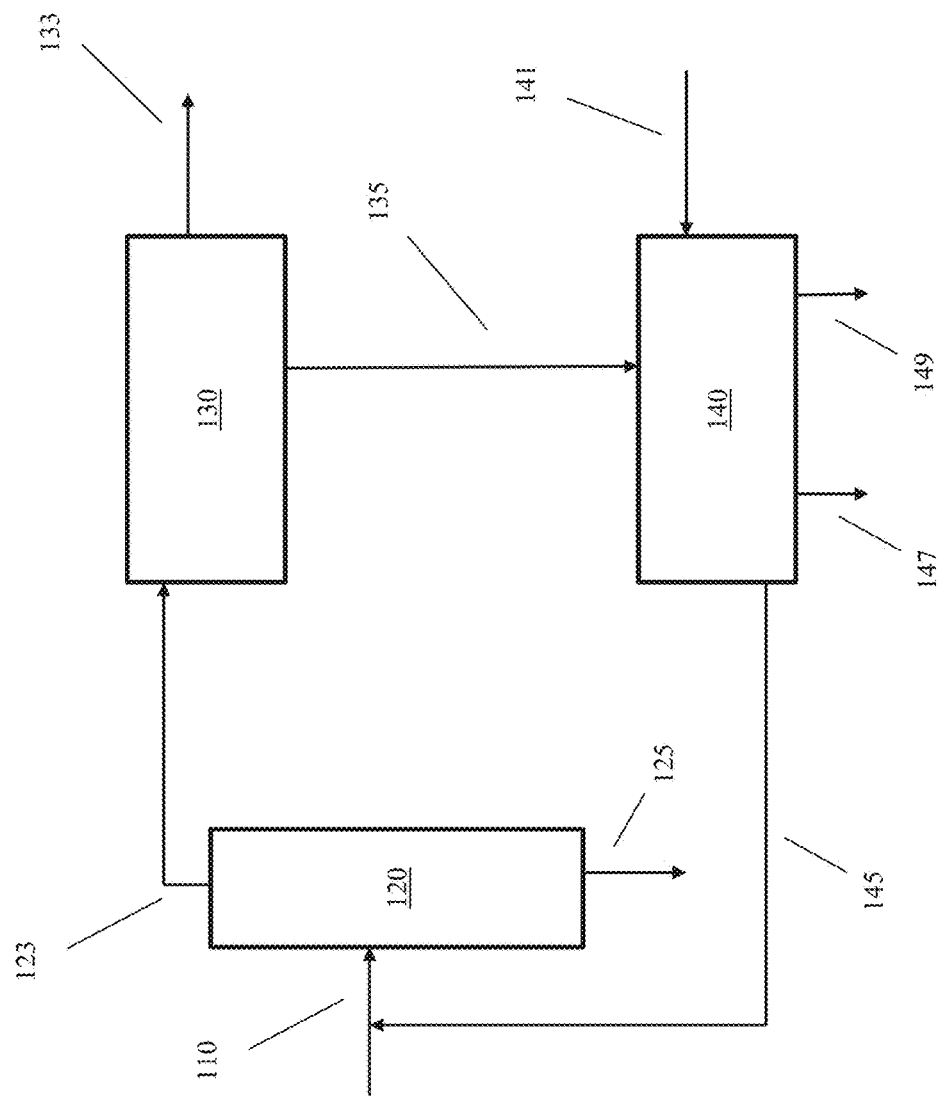
FIG. 1 schematically shows a process configuration for separation of a stream of higher purity para-xylene from a mixed aromatic input stream.

In various aspects, asymmetric membrane structures are provided that are suitable, for example, for hydrocarbon reverse osmosis of small hydrocarbons. In a specific example, an asymmetric membrane structure can have an amorphous pore network with a smallest or controlling pore size that is suitable for separation of para-xylene (p-xylene) from ortho-xylene (o-xylene) and meta-xylene (m-xylene). Methods for making an asymmetric membrane structure from polyvinylidene fluoride (or another partially fluorinated monomer) are also provided. An example of a suitable asymmetric membrane structure can be a hollow fiber membrane. When a polymer is used to form a membrane structure, the membrane structure can be subsequently cross-linked and/or pyrolyzed prior to use. In some aspects, cross-linking of the membrane structure can stabilize various portions of the membrane structure, so that desired properties are achieved and/or maintained during a subsequent pyrolysis step. In some aspects, a polymer can retain a desirable pore structure after pyrolysis without requiring prior cross-linking. Pyrolysis can then be used to convert the polymeric membrane structure to a porous carbon structure with a higher ratio of carbon to hydrogen.

In this discussion, the notation "$C_x$" refers to a hydrocarbon stream having at least 50 wt % of hydrocarbons containing "x" number of carbons. The notation "$C_{x+}$" refers to a hydrocarbon stream having at least 50 wt % of hydrocarbons containing "x" or more carbons. For these definitions, a hydrocarbon stream is defined to include streams where at least a portion of the compounds in the stream contain heteroatoms other than carbon and hydrogen.

In this discussion, a separation stage based on boiling point separation refers to a separation stage that includes one or more separators for performing a separation based on distillation, fractionation, flash separation, gas-liquid separation, and/or other separation methods where the composition of the resulting separated fractions is substantially dependent on the vapor pressures of the components of the feed to the separation stage at the separation conditions. This is in contrast to a membrane separation, which (depending on the nature of the feed) can potentially produce separated fractions that have substantially similar boiling ranges.

Asymmetric Membrane Structure

In various aspects, the membranes described herein can correspond to membranes having an asymmetric membrane structure. In an asymmetric membrane structure, a first membrane layer can correspond a porous support layer while a second membrane layer can correspond to a selective layer. The second membrane layer or selective layer can correspond to the layer that is exposed to a feed during a membrane separation. In aspects where a polymer is initially used to form at least a portion of a membrane structure, unless otherwise specified, the properties described in this section correspond to the properties of the membrane structure after any cross-linking and/or pyrolysis.

The second membrane layer or selective layer can have an amorphous interconnected pore structure. The amorphous interconnected pore structure can allow for selective separation of compounds based on molecular size under conditions suitable for hydrocarbon reverse osmosis. Because passage of permeating species through the selective layer is constrained during a separation, the selective layer can be relatively thin to maintain a desirable transport rate across the membrane. For example, the thickness of the selective layer can be about 0.08 µm to about 5 µm. Depending on the aspect the thickness of the selective layer can be about 0.1 µm to about 5 µm, or about 0.1 µm to about 3 µm, or about 0.1 µm to about 2.0 µm, or about 0.1 µm to about 1.5 µm, or about 0.1 µm to about 1.0 µm, or about 0.1 µm to about 0.5 µm.

To provide a sufficient number of pores for transport, the selective layer can have a surface area as measured by nitrogen adsorption (BET) of at least about 100 $m^2/g$, or at least about 200 $m^2/g$, or at least about 300 $m^2/g$, or at least about 500 $m^2/g$, or at least about 700 $m^2/g$ of pores having a pore size between 5 Angstroms and 100 Angstroms, or between 5 and 75 Angstroms, or between 5 and 50 Angstroms, or between 5 Angstroms and 35 Angstroms, or between 5 Angstroms and 20 Angstroms. In particular, the selective layer can have a surface area of at least about 300 $m^2/g$, or at least about 500 $m^2/g$, of pores having a pore size between 5 and 75 Angstroms, or between 5 and 35 Angstroms, or between 5 and 20 Angstroms. The pores in the selective layer can have any type of pore size distribution, such as a unimodal distribution, a bimodal distribution, or a multi-modal distribution.

Based in part on the interconnected nature of the amorphous pore structure, the transport characteristics of the selective layer can be defined based on the substantial pore size peak in the pore size distribution (such as pore width distribution) corresponding to the smallest median pore size. A substantial pore size peak is defined herein as a peak in a pore size distribution corresponding to at least 5 vol % of the pore volume. The pore size corresponding to a maximum height of a pore size peak in the pore size distribution can be referred to as a median pore size. The width of a pore size peak can be characterized based on the width of a pore size peak at half of the maximum height.

For separation of ortho-xylene and/or meta-xylene from para-xylene and/or ethylbenzene, the selective layer can have a substantial pore size peak corresponding to a smallest median pore size of about 5.8 Angstroms to about 6.8 Angstroms, or about 6.0 Angstroms to about 7.0 Angstroms, or about 6.0 Angstroms to about 6.8 Angstroms. As an example, a selective layer can have a substantial pore size peak corresponding to a smallest median pore size of about 6.0 Angstroms to about 6.5 Angstroms, such as about 6.2 Angstroms.

It is noted that the various pore sizes described above correspond to pore sizes present in the selective layer both when the membrane structure is exposed to a liquid and when a liquid is not present. For example, the substantial pore size peak corresponding to the smallest median pore size can have a size when a liquid for separation is present that differs by 10% or less, or 5% or less, or 2% or less from the size when the membrane structure is not exposed to a liquid for separation. This is in contrast to various "swellable" polymer membrane structures that exhibit a change (typically increase) in pore size when exposed to a liquid for separation. A liquid for separation can correspond to a component being separated or to a solvent and/or carrier for components being separated. Examples of suitable solvents include, but are not limited to, water, hydrocarbons that are a liquid at 25° C. and 1 bar (100 kPa), alcohols that are a liquid at 25° C. and 1 bar (100 kPa), or combinations thereof.

Another way of characterizing the amorphous pore network can be based on the width of the substantial pore size peak corresponding to the smallest median pore size. The width of the pore size distribution for the smallest median pore size can impact the ability of the selective layer to act as a separation membrane. For an effective separation, the width of the smallest median pore size peak can be characterized relative to the difference in the molecular diameters of the target compounds being separated. In some aspects, the width of the substantial pore size peak corresponding to the smallest median pore size (i.e., at half of the peak height) can be about 75% or less of the difference in molecular diameter between target compounds for separation, or about 60% or less, or about 50% or less, or about 40% or less. The target compounds for separation can also be defined in part based on the relative molecular diameters and the relative molecular weights of the compounds. For separations of ortho-xylene and/or meta-xylene from para-xylene and/or ethylbenzene, the difference in molecular size of the separation components is about 1.1 Angstroms or less. It is noted that these target compounds have approximately the same molecular weight (i.e., the molecular weights for separation differ by less than 0.1 g/mol).

The first layer can provide structural support for the second layer while having a sufficiently open pore network to allow for viscous flow across the first layer within the pore structure. This can correspond to having a median pore size in the first layer of at least about 20 nm, but any convenient pore size up to tens of microns can potentially be suitable so long as the porous structure is structurally stable under reverse osmosis conditions. In some aspects, a suitable pore volume for the first layer can be at least about 0.2 cm$^3$/g, or at least about 0.3 cm$^3$/g. The thickness of the first layer can be any convenient thickness that provides suitable structural support, such as 20 microns to 200 microns.

Another indicator of structural integrity can be the storage modulus for the membrane structure. In various aspects, the membrane structure can have a storage modulus of at least about 100 MPa, or at least about 200 MPa, or at least about 300 MPa, or at least about 400 MPa, at a temperature of 100° C., or a temperature of 200° C., or a 300° C.

Depending on the nature of how the membrane structure is fabricated, a transition region can be present between the second selective layer and the first support layer. The transition region can have any convenient thickness, but typically will be on the order of a few microns or less. In some aspects, the transition region can have a gradient of pore properties that transitions from the properties of the second selective layer to the properties of the first support layer.

Another way of characterizing a membrane structure is from single component transport studies. One use for single component transport studies is to characterize the defect density of a membrane. In various aspects, the membrane structures described herein can correspond to membrane structures with low defect densities. Without being bound by any particular theory, it is believed that membrane structures composed of partially fluorinated polymers can be formed with low defect densities, such as by spinning of a partially fluorinated polymer to form a hollow fiber membrane structure. The low defect density from the partially fluorinated polymer membrane structure can be carried over to a porous carbon membrane structure that is formed after pyrolysis. The pyrolysis of a partially fluorinated polymer membrane structure and/or cross-linking of such a membrane structure may also assist with reducing the number of defects present in a membrane structure. More generally, a variety of polymer membrane structures can provide a suitably low defect density after conversion to porous carbon membrane structures (such as by pyrolysis) when an appropriate support layer is available.

Defects provide nonselective permeation pathways through a membrane, which can diminish, reduce, or minimize the selectivity of a membrane for a desired separation. Flow through these nonselective permeation pathways can increase significantly as the transmembrane pressure is increased. This increase is proportionally faster than the increase in transmembrane pressure. Defect density in a membrane structure can be characterized by permeation studies in which the feed is pressurized and the permeate is drawn off at atmospheric pressure ($p^{permeate}$~14.7 psi). The temperature of the study can be chosen such that the feed and permeate are in the liquid phase. Preferred temperatures for the study can be between 0° C. and 200° C.; or 10° C. and 150° C.; or 20° C. and 100° C.; or 25° C. and 75° C. Molar flux, $\mathcal{N}_i$, (Mole/(Meter$^2$ Second) through the membrane is measured as a function of the feed pressure ($p^{feed}$) Initial feed pressures for the study can be selected so that $p^{feed}$ is at least 3 times greater than $p^{permeate}$ or at least 6 times greater than $p^{permeate}$, or preferably at least 10 times greater than $p^{permeate}$. In some aspects, the characterization can be started with as high a feed pressure as possible. This can be in a range from 200 to 800 psia or from 400 psia to 750 psia. In a high quality membrane with an acceptable number of defects, the permeance, $\mathcal{N}_i/(p^{feed}-p^{permeate})$ can increase by less than a factor of 5 when the feed pressure is doubled and by less than a factor of 10 when the feed pressure is quadrupled. In a higher quality membrane with fewer defects, the permeance, $\mathcal{N}_i/(p^{feed}-p^{permeate})$ can increase by less than a factor of 3 when the feed pressure is doubled or by less than a factor of 6 when the feed pressure is quadrupled. In a very high quality membrane with even fewer defects, the permeance, $\mathcal{N}_i/(p^{feed}-p^{permeate})$ can change by less than a factor of 2 when the feed pressure is doubled and by less than a factor of 4 when the feed pressure is quadrupled. In an even higher quality membrane with yet fewer defects, the permeance, $\mathcal{N}_i/(p^{feed}-p^{permeate})$ changes by less than a factor of 1.15 when the feed pressure is doubled and by less than a factor of 1.25 when the feed pressure is quadrupled. It is also possible to characterize the membrane quality using permeate pressures in a range between 0.5 and 10 bara, or 1 and 5 bara, so long as the permeate is in the liquid phase. Thus, membrane quality can generally be characterized for pressures between about 50 kPa and 1000 kPa, or between about 1.0 MPa and about 5.5 MPa, or between about 2.0 Mpa and about 5.0 MPa. In performing single component permeation studies to characterize the defect density of the membrane, it is generally preferred to use a molecule that has a minimum dimension slightly larger than the characteristic pore size of the membrane. In this discussion, a characteristic dimension of a membrane with an amorphous, interconnected membrane structure can correspond to the median pore size of the smallest substantial peak in the pore size (i.e. pore width) distribution. Ideally the minimum molecular dimension is about 0.5 to 0.6 Angstroms greater than the characteristic dimension of the pores in the membrane, or is about 1.0 to 1.2 Angstroms greater than the characteristic dimension of the pores in the membrane, or is about 2.0 to 2.2 Angstroms greater than the characteristic dimension of the pores in the membrane, or is about 5.0 to 5.3 Angstroms greater than the characteristic dimension of the pores in the membrane, or is about 10.0 to 10.4 Angstroms greater than the characteristic dimension of the pores in the membrane. The minimum dimension of a wide range of molecules has been documented in the literature. Additionally or alternatively, those skilled in the art can calculate the minimum molecular dimension using quantum chemical calculations. For a membrane with a characteristic size of about 6 Angstroms, ortho-xylene can be used to characterize the defect density, because it has a minimum molecular size of about 0.5 to 0.8 Angstroms greater than the characteristic size.

For a membrane with an acceptable number of defects, the pore size can also be characterized by performing single component permeation studies with two different sized molecules. The molecules are chosen to bracket the characteristic pores size of the membrane. For a membrane with a narrow pore size distribution the molecules can differ in their minimum dimension by 0.5 to 2 angstrom. For an acceptable reverse osmosis membrane, the ratio of single component permeances measured at the same temperature and pressure conditions with a transmembrane pressure, ($p^{feed} - p^{permeate}$), greater than 10 bara can be used to characterize the pore size distribution. In various aspects, the ratio of single component permeances can be greater than 2, preferably greater than 6, more preferably greater than 10, and even more preferably greater than 20 for at least one pair of molecules used to characterize the pore size distribution of the membrane. Optionally, the comparative single component permeation studies can be performed at higher transmembrane pressures, such as transmembrane pressures of at least 20 bara, or at least 30 bara, or at least 50 bara, or at least 100 bara. The width of the pore size distribution can then be taken from the smallest molecular size difference that produces an acceptable ratio of permeances. For a membrane with a characteristic size of about 5.8 Angstroms to about 7.0 Angstroms, such as at least about 6 Angstroms, a comparison of single component para-xylene and ortho-xylene permeation can be used to characterize the pore size. Membranes with a ratio of single component permeances measured at the same temperature and pressure conditions with a transmembrane pressure greater than 2 are considered to be selective, with a ratio greater than 10 they are considered to be very selective and with a ratio greater than 20 are considered to be extremely selective.

Example of Making an Asymmetric Structure—Hollow Fiber

One method for making an asymmetric membrane structure having a first (selective) layer and a second (porous support) layer can be to first make an asymmetric hollow fiber structure. A suitable material for forming an asymmetric hollow fiber structure is polyvinylidene fluoride (PVDF). Other partially fluorinated ethylene polymers, partially fluorinated propylene polymers, and partially fluorinate ethylene-propylene co-polymers can also be suitable materials. In this description, a partially fluorinated ethylene polymer is defined as an ethylene polymer having an average number of fluorines per monomer unit of 1 to 3. Similarly, a partially fluorinated propylene polymer is defined as a propylene polymer having an average number of fluorines per polymer backbone carbon pair of 1 to 3.

In other aspects, other types of polymers can also be suitable for formation of an asymmetric membrane structure. Other examples of suitable polymers can include, but are not limited to, polyimide polymers (such as Matrimid® 5218, available from Ciba Specialty Chemicals), polyamide-imide polymers (such as Torlon® polymers available from Solvay Specialty Polymers), polyetherimide polymers (such as Ultem® resins available from SABIC), and partially or fully fluorinated polyethylene and/or polypropylene polymers (or co-polymers), such as polyvinylidene fluoride or polytetrafluoroethylene. More generally, suitable polymers may include glassy polymers, polymers with high intrinsic microporosity, and/or polymers that when are known to form a porous carbon structure when the cross-linked polymer is exposed to pyrolysis conditions.

A hollow fiber asymmetric membrane structure can be formed by using a co-annular spinneret with two types of PVDF solutions (or other partially fluorinated polymer solutions). In a dual-layer hollow fiber spinning process, polymer solutions comprising solvent, non-solvent, and polymer can be prepared. For the core polymer solution, dimethylacetamide (DMAc) can be used as a solvent and mixture of lithium chloride (LiCl) and water can be used as non-solvents. For the sheath polymer solution, a mixture of dimethylacetamide and tetrahydrofuran can be used as solvents and ethanol can be used as a non-solvent. For both core and sheath polymer solutions, poly(vinylidene) fluoride can be used as a polymer source. Asymmetric double layer hollow fibers can be created via nonsolvent phase inversion technique, which is known as dry jet wet-quench spinning. The aforementioned polymer solutions can be extruded through a spinneret into a non-solvent quench bath and further taken-up on a spinning drum at desired speed.

In various aspects, the sheath layer and core layer in a hollow fiber structure can be further processed to form a second layer and first layer as described above. Examples of suitable processing can include cross-linking of the polymer and pyrolysis of the cross-linked polymer. Prior to the further processing, the core layer can be a porous layer similar to the porous or first layer of the membrane structure. In some aspects, the pore volume of the core layer prior to further processing can be at least about 0.02 cm$^3$/g, with the pore volume corresponding to pores with a median pore size of at least about 20 nm. Prior to the further processing, the sheath layer can be a dense layer, but the sheath layer can have a different pore structure than the second layer as described above. For example, when PVDF is used as the polymer, the sheath layer prior to further processing can have a surface area (BET nitrogen adsorption) of about 100 m$^2$/g or less, or about 50 m$^2$/g or less, or about 30 m$^2$/g or less. This type of low surface area can indicate a sheath layer with limited permeability due to the limited availability of pores.

Cross-Linking of Polymer Structure

In aspects where an asymmetric membrane structure is formed using a polymer, such as a polymer formed from partially fluorinated ethylene or propylene, the membrane structure can be cross-linked. Any convenient cross-linking method suitable for cross-linking of both the first dense (sheath) layer and the second porous (core) layer can be used.

An example of a suitable cross-linking method can be to immerse the membrane structure in a methanol-based cross-linking solution. The cross-linking solution can be formed by dissolving sodium hydroxide and p-xylylenediamine in methanol. Additionally, magnesium oxide powders can be added to the solution as an HF sink. The membrane structure can be immersed into the solution and slowly stirred at room temperature for a desired period of time, such as 12 hours to 96 hours. In some aspects, selection of a different cross-linking agent may result in a different smallest median pore size in the selective layer.

Prior to and/or after cross-linking the membrane structure (such as a hollow fiber structure) can be solvent exchanged and dried. Examples of suitable fluids for solvent exchange are methanol and water. An example of a drying procedure can be drying under a pressure of less than 100 kPa, or less than 10 kPa, or less than 1 kPa, at a temperature between 50° C. and 150° C.

Pyrolysis of Polymer Membrane Structure

After any optional cross-linking, a polymer membrane structure can be pyrolyzed. Pyrolysis of the polymer membrane structure can convert a least a portion of the polymer structure to a more carbonaceous material. In other words, the carbon to hydrogen ratio in the membrane structure can be increased. After pyrolysis, the layers of the membrane structure can be referred to as porous carbon layers. Depending on the pore size, the selective layer can alternatively be referred to as a carbon molecular sieve.

Pyrolysis can be performed by heating the membrane structure in an inert atmosphere, such as an atmosphere comprising nitrogen and/or a noble gas (e.g. argon). The atmosphere can have a reduced or minimized content of oxygen, such as less than 50 vppm, or less than 10 vppm. During pyrolysis, the membrane structure can be heated in the inert atmosphere according to a desired heating profile until a target temperature is achieved. The target temperature for pyrolysis can be between 400° C. to 650° C. For example, the pyrolysis temperature can be at least about 400° C., or at least about 450° C., or at least 500° C., or at least 550° C., and/or about 650° C. or less, or about 600° C. or less. The target temperature can be maintained for a period of time, such as 0.5 hours to 5 hours. The heating profile for achieving the target temperature can be any convenient profile. Optionally, the heating profile can include multiple heating rates. For example, the initial temperature ramp can be at a higher rate, such as 10° C./min, with the temperature ramp being reduced to one or more lower values as the temperature in the pyrolysis oven approaches the target temperature. In general, the temperature ramp rate can range from 0.1° C./min to 25° C./min with as many temperature ramp rates as desired, depending on the nature of the desired profile. Optionally, the heating profile can maintain one or more temperatures other than the target pyrolysis temperature for a period of time.

Example of Making an Asymmetric Structure—Porous Metal Support

In the prior example, a dual layer hollow fiber structure was formed by using a dual-layer spinning process. Another option for making an asymmetric structure can be to first form a hollow fiber structure and then add a coating layer to provide the asymmetric structure. This can allow for separate processing conditions for the core or first layer and the additional coating layer, such as higher severity conditions for the core layer or higher severity conditions for the additional coating layer.

When forming an asymmetric structure by first forming a hollow fiber structure and then adding a coating layer, the initial hollow fiber structure can correspond to a metal or metal-enhanced fiber structure. For example, metal particles can be mixed with a binder, such as a polymer binder, for extrusion using a hollow fiber spinning system. The resulting extruded hollow fiber can then be calcined/sintered to remove the binder and form a porous metal structure. More generally, a porous metal structure can be formed using any convenient type of process that allows for extrusion (or other formation) of a layer or other structure. For example, a mixture of metal particles and polymer binder can be extruded to form a sheet of a desired thickness. The sheet can then be calcined as described below to remove the polymer portion and form a porous metal support structure having (roughly) the shape of the extruded sheet. An asymmetric structure can then be formed by depositing a coating layer of a desired polymer on the sheet of porous metal support structure. As another example, a mixture of metal particle and polymer binder can be cast to form a structure having a desired shape, such as a hollow fiber shape. After calcining/sintering to form a porous metal structure, a coating layer of a polymer can be added to surface of the porous metal structure to allow for formation of an asymmetric membrane structure.

Suitable metal particles can include, but are not limited to, metal particles comprising and/or composed of stainless steel, nickel, chrome, copper, silver, gold, platinum, palladium, and combinations thereof. The metal particles can have an average characteristic length of about 2.0 µm to about 5.0 µm. For particles having a roughly spherical shape, including shapes such as ellipsoids or ovoids, the characteristic length can correspond to a length of the particle along at least one axis for the particle. Examples can include a diameter for a sphere or the length along the major axis of an ellipse. For particles having an irregular shape and/or having a cylindrical type shape (with one axis being substantially larger than another axis), the characteristic length can correspond to the largest length associated with any orientation of the particle. It is noted that the characteristic length for the particles can influence the pore size in the resulting porous metal porous support.

Polymers can be a suitable binder for the metal particles. Examples of suitable binders can include, but are not limited to, partially fluorinated polymers as described above. The amount of metal particles to binder can be any convenient amount that allows for extrusion of the mixture of metal particles and binder. In various aspects, the volume ratio and/or weight ratio of metal to binder in the mixture can be from about 0.5 (more binder than metal) to about 5. The mixture of metal and binder can correspond to a precursor composition.

After extrusion or casting to form a hollow fiber, a flat layer or sheet, or another extruded/cast structure, the extruded/cast structure can be calcined and/or sintered under suitable conditions to form a porous metal (membrane) structure. The sintering for forming the porous metal structure can correspond to a partial sintering. During calcination, the polymer (or other binder) portion of the precursor composition can be removed. During and/or after removing the binder, sintering can be performed to allow the metal particles to flow together to form the porous metal structure. The porous metal membrane structure can be optionally sintered for additional time. The resulting porous metal structure can then substantially remain in an unchanged form during subsequent deposition/formation of a selective layer. The porous metal structure can correspond to the second or structural support layer of an eventual dual layer membrane structure. After calcining and/or sintering, the porous metal structure can have an average pore size of about 0.5 to about 5.0 µm. After calcining and/or sintering, the porous metal membrane structure can have the other properties identified above for a second or structural support layer.

Calcining and/or sintering of an extruded/cast structure can be performed at a temperature that is suitable for decomposition of the polymer or other binder. The temperature for calcining and/or sintering can also be suitable for sintering of the metal particles to form a continuous membrane structure (i.e., the porous metal membrane structure). In some aspects, calcining and sintering can be performed according to a single temperature program or profile for heating of the extruded/cast structure. In such aspects, sintering can be used to refer to both the calcination for polymer/binder decomposition and the sintering of the metal particles.

In aspects where separate calcination and sintering processes are performed, the calcination temperature can be about 400° C. to about 800° C., or about 450° C. to about 700° C. Calcining can be performed in an oxygen-containing atmosphere that can facilitate decomposition of the polymer or other binder. The calcining can be performed for a convenient period of time that is suitable for decomposition or other removal of the binder, such as about 10 minutes to about 10 hours, or about 1 hour to about 8 hours. During and/or after removal of the polymer or other binder, the metal particles can be sintered to form the porous metal structure. Sintering conditions can include a temperature of about 800° C. to about 1300° C., or about 900° C. to about 1200° C. The sintering atmosphere can be an oxygen-containing atmosphere or an inert atmosphere, such as a nitrogen or noble gas atmosphere. The sintering can be performed for about 1 hour to about 24 hours. It is noted that formation of the porous metal membrane structure does not require a sintering temperature that is above the melting point of the metal. Optionally, the sintering conditions can be substantially similar to the calcining conditions.

One option for increasing the temperature of an extruded/cast structure can be to increase the temperature of the extruded structure according to a temperature program or profile. A temperature program can include a series of program steps. As an example, a temperature program for sintering an extruded layer at 1100° C. can start with a first temperature ramp rate of about 5° C./min at temperatures between 50° C. and 200° C. The temperature ramp rate can then be reduced to about 1° C./min between 200° C. and 300° C. The temperature ramp rate can then be increased to about 5° C./min between 300° C. and 400° C. The temperature ramp rate can then be reduced to about 1° C./min between 400° C. and 600° C. The temperature ramp rate can then be increased to about 5° C. between 600° C. and 1100° C. When a temperature of about 1100° C. is achieved, the temperature can then be maintained for a desired period of time, such as about 60 minutes. Of course, other combinations of ramp rates, temperatures for changing the ramp rate, final temperature, and/or length of time at the final temperature can be used. Additionally or alternately, one or more additional temperature plateaus (i.e., ramp rate of about 0° C./min) can also be included prior to achieving the final temperature. Such plateaus can be maintained for a convenient or desired length of time. Additionally or alternately, the final temperature of the temperature program can be lower than a temperature achieved earlier in the temperature program.

After forming the porous metal structure, a polymer layer can be formed on the porous metal structure, such as by deposition. The deposited polymer layer can become a selective layer for a dual layer membrane structure. Without being bound by any particular theory, it is believed that because the porous metal structure can provide a structurally and chemically stable support layer, the conditions for forming the selective layer can be less severe. Additionally, the support from the support layer can potentially assist the selective layer in maintaining structural integrity during the formation of the selective layer. These features can allow for formation of selective layers using polymers that might not be suitable for direct formation of a dual layer hollow fiber structure as described above. For example, polyimide materials such as Matrimid® polymers can be suitable for forming a selective layer on a porous metal support layer. Because the porous metal structure is calcined in advance, the porous metal structure can provide support for the selective polymer layer during formation of the carbon membrane pore network. For example, one potential difficulty with forming an asymmetric hollow fiber structure can be that the selective layer can plasticize and collapse prior to final annealing/pyrolyzing of the hollow fiber structure. Cross-linking can help in avoiding this outcome, but requiring the use of polymers that form a suitable selective layer after cross-linking can restrict the types of selective layers that can be formed. Using a porous metal membrane support can enable a selective (polymer) layer to plasticize and collapse during annealing/pyrolyzing of the selective layer to form a carbon membrane while remaining suitable thin to serve as a selective layer. This can allow for use in the selective layer of polymers that are not cross-linked, so long as the non-cross-linked polymers can form a carbon membrane structure with a stable pore network.

Matrimid® polymers can be used to form a selective layer having a roughly 3-4 Angstrom size for the pore network. Other examples of suitable polymers for forming a selective layer can include, but are not limited to, polyimide polymers (such as Matrimid® 5218, available from Ciba Specialty Chemicals), polyamide-imide polymers (such as Torlon® polymers available from Solvay Specialty Polymers), polyetherimide polymers (such as Ultem® resins available from SABIC), and partially or fully fluorinated polyethylene and/or polypropylene polymers (or co-polymers), such as polyvinylidene fluoride or polytetrafluoroethylene. More generally, suitable polymers may include glassy polymers, polymers with high intrinsic microporosity, and/or polymers that when are known to form a porous carbon structure when the cross-linked polymer is exposed to pyrolysis conditions.

One option for depositing a polymer layer on a porous metal structure can be to use a dip coating process. The porous metal structure can be immersed in a polymer solution containing the desired polymer for the selective layer. The porous metal structure can then be withdrawn at a convenient rate to allow for formation of a coating layer of a desired thickness on the porous metal membrane structure. In some aspects, convenient pull rate for dip coating can correspond to about 1 cm/sec to about 10 cm/sec. As an example, a porous metal structure corresponding to a hollow fiber can have a polymer layer deposited on the exterior of the hollow fiber by dip coating. An end of the hollow fiber can correspond to a sealed end. A sealed end can be formed by any convenient method, such as by physically sealing the end with an epoxy or other sealing material. The hollow fiber can be dipped into a polymer solution starting with the sealed end so that a coating layer is formed on the exterior of the hollow fiber.

The coating layer formed on the porous metal structure can then be dried and/or pyrolyzed to form the selective layer. Drying can correspond to an optional initial process where solvent is removed from the coating layer at temperatures of about 100° C. or less and optionally at pressures below about 100 kPa-a. Pyrolysis can be performed by heating the membrane structure in an inert atmosphere, such as an atmosphere comprising nitrogen and/or a noble gas (e.g. argon). The atmosphere can have a reduced or minimized content of oxygen, such as less than 50 vppm, or less than 10 vppm. During pyrolysis, the membrane structure can be heated in the inert atmosphere according to a desired heating profile until a target temperature is achieved. The target temperature for pyrolysis can be between 400° C. to 650° C. For example, the pyrolysis temperature can be at least about 400° C., or at least about 450° C., or at least 500° C., or at least 550° C., and/or about 650° C. or less, or about 600° C. or less. The target temperature can be maintained for a period of time, such as 0.5 hours to 5 hours. The heating profile for achieving the target temperature can be any convenient profile. Optionally, the heating profile can include multiple heating rates. For example, the initial temperature ramp can be at a higher rate, such as 10° C./min, with the temperature ramp being reduced to one or more lower values as the temperature in the pyrolysis oven approaches the target temperature. In general, the temperature ramp rate can range from 0.1° C./min to 25° C./min with as many temperature ramp rates as desired, depending on the nature of the desired profile. Optionally, the heating profile can maintain one or more temperatures other than the target pyrolysis temperature for a period of time.

As an example, a temperature program for pyrolysis at 500° C. can start with a first temperature ramp rate of about 10° C./min at temperatures between 50° C. and 250° C. The temperature ramp rate can then be reduced to about 4° C./min between 200° C. and 485° C. The temperature ramp rate can then be further reduced to about 0.2° C./min between 485° C. and 500° C. When a temperature of about 500° C. is achieved, the temperature can then be maintained for a desired period of time, such as about 120 minutes. Of course, other combinations of ramp rates, temperatures for changing the ramp rate, final temperature, and/or length of time at the final temperature can be used. Additionally or alternately, one or more additional temperature plateaus (i.e., ramp rate of about 0° C./min) can also be included prior to achieving the final temperature. Such plateaus can be maintained for a convenient or desired length of time. Additionally or alternately, the final temperature of the temperature program can be lower than a temperature achieved earlier in the temperature program.

Pyrolysis of the coating layer can result in formation of an asymmetric membrane structure. The asymmetric membrane structure can be substantially free of mesopore defects. One option for characterizing an asymmetric membrane structure with regard to mesopore defects can be to determine relative rates of He and $N_2$ permeability in a constant pressure gas permeation system. For example, single component gas phase permeation data can be collected at a membrane upstream pressure of about 100 psia (~700 kPa-a) and a temperature of about 35° C. Single component gas phase permeation rates can then be determined for two different components, such as He and $N_2$. The ratio of the He permeation rate to the $N_2$ permeation rate can then be compared with the Knudsen selectivity for He/$N_2$ permeation through large pores at low pressures of about 3.7. In various aspects, the ratio of permeation rates for He versus $N_2$ for an asymmetric membrane structure can be at least about 8.0, or at least about 10, or at least about 12, such as up to about 100 or more.

Another option for characterizing an asymmetric membrane structure can be based on single component liquid phase permeation. For example, an asymmetric membrane structure can be immersed and/or filled with a liquid of interest for permeation. The selective layer side of the asymmetric membrane structure can then be pressurized at a constant pressure using the liquid. During pressurization, it may be desirable to limit the pressurization rate to less than a threshold value, such as less than about 200 kPa/min, in order to reduce or minimize the possibility of membrane failure during pressurization. Steady state flux at a pressure can then be measured over time to determine a liquid phase permeation rate for the liquid.

As an example, a precursor structure (metal particles plus binder) for a stainless steel porous fiber substrate can be extruded as described above. The extrusion can include passing/extruding the structure through capillary quartz tubing to obtain a straight stainless steel substrate. The precursor structure can be calcined at ~600° C. for ~30 minutes to remove carbon from the polymer binder while minimizing oxidation. More generally, the full temperature profile for performing the calcination can be selected so that the overall shrinkage of the stainless steel structure (length and diameter) is about 65%. The resulting stainless steel substrate can then be dip coated as described above. Prior to dip coating, the substrate can be pre-soaked with a non-polar (neutral) solvent. The dip coating solution can correspond to, for example, a solution containing about 18 wt % PVDF in about 70 wt % of a solvent, such as tetrahydrofuran. The dip coating can be performed at an elevated temperature, such as 50° C. to 100° C. After dip coating, a water wash can be performed at a similar elevated temperature. The PVDF layer formed on the substrate can then be cross-linked, as described above. After removing the structure from the cross-linking environment, the structure can be washed by flushing the structure multiple time with warm deionized water to remove excess base. This can avoid exposing the stainless steel substrate to an acidic environment. Finally, the cross-linked polymer structure can be exposed to pyrolysis conditions as described above to form an asymmetric membrane structure, where the selective layer corresponds to the carbon membrane formed during pyrolysis and the substrate or support layer corresponds to the stainless steel layer or structure.

Hydrocarbon Reverse Osmosis

An asymmetric membrane as described herein can be used for performing membrane separations based on hydrocarbon reverse osmosis. Hydrocarbon reverse osmosis generally refers to a selective membrane separation where a separation is performed on hydrocarbon liquid containing at least two hydrocarbon or hydrocarbonaceous components. Hydrocarbonaceous components refer to compounds containing carbon and hydrogen that may also contain heteroatoms, such as oxygen or nitrogen. In some aspects, hydrocarbonaceous compounds are defined to include compounds having up to roughly equal numbers of carbons and heteroatoms (i.e., atoms different from carbon or hydrogen). Examples of hydrcarbonaceous compounds having roughly equal numbers of carbons and heteroatoms can include, but are not limited to, sugars and/or other carbohydrates. In some alternative aspects, hydrocarbonaceous compounds used as components in a reverse osmosis or forward osmosis separation can be limited to hydrocarbonaceous compounds having fewer heteroatoms than carbons.

The process is executed such that the hydrocarbon or hydrocarbonaceous components being separated are in the liquid phase in both the feed and permeate. In this discussion, a reverse osmosis process is defined as a process such that for at least one position along the length of the membrane, the hydrocarbon molecules (and/or hydrocarbonaceous molecules) being separated are in the liquid phase in both the feed and the permeate. In some aspects, there may be other components in the feed that depending on concentration, temperature, and pressure, can produce a two phase liquid/gas mixture in either the feed or permeate. Examples of gaseous molecular species that can be present that are not hydrocarbons or hydrocarbonaceous include hydrogen, nitrogen, carbon dioxide, carbon monoxide, hydrogen sulfide. Other light hydrocarbon components such a methane, ethane, ethylene, propane or butane can depending on pressure, temperature, and concentration produce a two phase liquid/gas mixture in either feed or permeate. Another non-hydrocarbon that can be present is water or water vapor.

Based on the interconnected nature of the amorphous pore network, the substantial pore size peak having the smallest median pore size for the pore network can determine the effective size of compounds that can pass through the selective layer. A first component having a molecular size less than the smallest median pore size of the pore network can selectively pass through the selective layer of the membrane structure, while a second component having a molecular size greater than the smallest median pore size can pass through the selective layer in a reduced or minimized amount.

In hydrocarbon reverse osmosis, a first hydrocarbon (or hydrocarbonaceous) component is separated from a second hydrocarbon (or hydrocarbonaceous) component based on a molecular size differential. Without being bound by any particular theory, it is believed that based on the nature of an interconnected amorphous pore network, permeating species have multiple diffusional routes through the network thus enabling faster/smaller diffusing molecules to pass slower/larger ones either through larger pores or through connected alternate pathways. This is in contrast to a crystalline pore structure, where the pore channels can become clogged by slower diffusing/larger molecules. This contrast is particularly important in liquid phase separations where pores are fully loaded with the permeating species.

In order to perform a reverse osmosis separation, the pressure on the feed side of the membrane structure can be sufficiently large to overcome the "osmotic pressure", or the driving force that can tend to cause a higher purity solution to transfer material to a lower purity solution across a membrane. At pressures below the osmotic pressure, the amount of permeate transferred across the membrane can be limited. The osmotic pressure for a hydrocarbon (or hydrocarbonaceous) component can be dependent on the nature of the component and the concentration of the component in the feed to the membrane. Examples of suitable feed pressures for overcoming the osmotic pressure can be at least about 30 bar (3.0 MPa), or at least about 35 bar (3.5 MPa), or at least about 40 bar (4.0 MPa), or at least about 50 bar (5.0 MPa), and/or up to about 200 bar (20 MPa) or less, or about 170 bar (17 MPa) or less, or about 150 bar (15 MPa) or less.

In selective hydrocarbon reverse osmosis, the liquid phase mole fraction of at least one hydrocarbon and/or hydrocarbonaceous component can be greater in the permeate than in the feed. In some aspects, the mole fraction of this component in the liquid phase can be at least 200% greater in the permeate when the molar concentration in the feed is in a range from 0.1% to 10%, 100% greater in the permeate when the molar concentration in the feed is in a range from 10% to 20%, 75% greater in the permeate when the molar concentration in the feed is in a range from 20% to 40%, 50% greater in the permeate when the molar concentration in the feed is in a range from 40% to 60%, 20% greater in the permeate when the molar concentration in the feed is in a range from 60% to 80%, and 10% greater in the permeate when the molar concentration in the feed is in a range from 80% to 90%. Preferably, the mole fraction of this component in the liquid phase can be at least 500% greater in the permeate when the molar concentration in the feed is in a range from 0.1% to 10%, and 250% greater in the permeate when the molar concentration in the feed is in a range from 10% to 20%.

Another metric for membrane performance can be the selectivity of a pair of hydrocarbon or hydrocarbonaceous components in the feed. The binary selectivity is defined as the ratio of their molar concentrations in the permeate flowing out of the membrane module divided by the concentration in the feed. For a pair of molecules A and B, the molecules can be chosen so that the selectivity is greater or equal to 1 with:

$$\text{Selectivity} = [\chi_A(\text{Permeate})/\chi_B(\text{Permeate})]/[\chi_A(\text{Permeate})/\chi_A(\text{Permeate})]$$

where $\chi_A$(Permeate) is the mole fraction of A in the permeate, $\chi_B$(Permeate) is the mole fraction of B in the permeate, $\chi_A$(Feed) is the mole fraction of A in the feed, and $\chi_B$(Feed) is the mole fraction of B in the feed. It is preferred that the membrane be operated in a reverse osmosis process such that there is at least one pair of hydrocarbon and/or hydrocarbonaceous components for which the selectivity is greater than 2, or 5, or 10, or 20, or 40, or 100. This can be achieved using a membrane a) that has a smallest median pore size in a range that can separate molecules A and B, b) that has a low defect density, and c) that can be operated with a transmembrane pressure sufficiently high to provide thermodynamic drive for selective permeation. Transmembrane pressures can be at least about 10 bar, or at least about 20 bar, or at least about 50 bar, or at least about 100 bar. Optionally but preferably, the flow rate of the feed across the membrane can be fast enough so that a selective separation will occur at a reasonable commercial time scale.

For hydrocarbon reverse osmosis, the feed can flow over the membrane at a pressure at least 2 bars greater than the pressure at which the permeate is drawn off. More preferably the feed is at a pressure at least 5 bars greater than the permeate pressure, or at least 10 bars greater than the permeate pressure, or at least 50 bars greater than the permeate pressure, or at least 100 bars greater than the permeate pressure, or at least 200 bars greater than the permeate pressure. It is preferable that the flux of the molecular species being selectively transported through the membrane increase as the transmembrane pressure (pressure difference between the feed and permeate) increases from 2 bar to 5 bar, or 2 bar to 10 bar, or 2 bar to 20 bar, or 2 bar to 100 bar.

As noted and defined above, in a reverse osmosis separation the hydrocarbon and/or hydrocarbonaceous species being separated are in the liquid phase on both the feed and permeate sides of the membrane for at least one point along the length of the membrane. In one mode of operation the hydrocarbon or hydrocarbonaceous species being separated are in the liquid phase of the feed being introduced into the membrane module and at least one of the species being separated is predominantly in the liquid phase of the permeate being drawn out of the membrane module. Pressure in the permeate can be sufficient so that the hydrocarbon species are in the liquid phase for at least one point along the permeate side of the membrane. Permeate pressure can be 0.25 bara or greater. In one mode of operation the permeate pressure can be in a range from 1 to 5 bara, which can reduce, minimize, or eliminate the need for a vacuum on the permeate side of the membrane.

In various aspects, the temperature for a hydrocarbon reverse osmosis separation can be any convenient temperature from about 0° C. to about 300° C. The temperature for a given separation can be dependent on the nature of permeate component and the nature of the retentate. Depending on the aspect, the separation temperature can be about 0° C. to about 100° C., or about 50° C. to about 150° C., or about 100° C. to about 200° C., or about 150° C. to about 250° C., or about 200° C. to about 300° C. Alternatively, the separation temperature can be at least about 0° C., or at least about 25° C., or at least about 50° C., or at least about 75° C., or at least about 100° C., or at least about 125° C., or at least about 150° C., or at least about 175° C., or at least about 200° C., and/or about 300° C. or less, or about 275° C. or less, or about 250° C. or less, or about 225° C. or less, or about 200° C. or less, or about 175° C. or less, or about 150° C. or less, or about 125° C. or less, or about 100° C. or less.

As described above, the amorphous pore network of the membrane structure can allow for separation under reverse osmosis conditions. Another consideration for the membrane structure can be providing sufficient structural stability to maintain the integrity of the membrane structure under reverse osmosis conditions. At least a portion of the structural support for the membrane structure can be provided by the second porous layer. Optionally, additional support can be provided by using additional non-membrane materials to support or package the membrane structure.

Another option for providing additional structural integrity can be to use a hollow fiber membrane structure. The annular nature of a hollow fiber membrane structure can allow the membrane structure to be self-supporting. In one example of a configuration, a plurality of hollow fiber membrane structures can be located in a separation volume. A feed for separation can be introduced into the volume. The permeate from the membrane separation can enter the hollow bores of the hollow fiber membranes. The permeate within the bores of the hollow fibers can then be transported out of the separation volume.

A variety of hydrocarbon separations can potentially be performed as hydrocarbon reverse osmosis separations as described herein. Examples of potential separations include, but are not limited to:

1) Separation of para-xylene from o-xylene and m-xylene. Para-xylene has a molecular diameter of about 5.8 Angstroms, while o-xylene and m-xylene have diameters of about 6.8 Angstroms.

2) Separation of para-xylene from para-diethylbenzene. In simulated moving bed separators for separation of para-xylene from other $C_8$ compounds, para-diethylbenzene is used to displace para-xylene in the bed during desorption. While this separation can be performed by distillation, a reverse osmosis separation could allow for recovery of additional p-xylene from the para-diethylbenzene desorbent.

Configuration Example: Xylene Separations

FIGS. 1 to 4 schematically show an example of how a xylene separation/purification loop can be modified using membrane structures as described herein. FIG. 1 shows an example of a typical para-xylene recovery loop. In FIG. 1, an input stream 110 comprising a mixture of $C_{8+}$ aromatics is passed into a distillation column 120 for separation of higher boiling point compounds 125 (i.e., $C_{9+}$) from $C_8$ compounds 123. A $C_{8+}$ isomerate stream 145 can be added to input stream 110 prior to introduction into distillation column 120. It is noted that the stream of $C_8$ compounds 123 typically includes ethylbenzene. Stream of $C_8$ compounds 123 is then passed into a para-xylene recovery unit 130 for separation into a higher purity para-xylene stream 133 and a raffinate or filtrate 135 that is depleted in para-xylene. Para-xylene recovery unit 130 can be, for example, a simulated moving bed separator. The raffinate 135 can be introduced into isomerization unit 140 for conversion of ortho- and meta-xylene into the desired para-xylene product. Isomerization unit 140 can also receive a hydrogen input stream 141. The isomerized effluent 145 can include $C_8$ isomerates as well as other side products. For example, depending on the nature of the feed, isomerization unit can optionally generate additional side products, such as a benzene/toluene stream 147 and/or light gas 149 that can be generated during cracking of ethylbenzene. These $C_{7-}$ products can be separated from isomerized effluent 145 using, for example, an optional additional ditillation column 128. The remaining fraction from the optional additional distillation column 128 can correspond to a $C_{8+}$ isomerate stream. During the process in isomerization unit 140, if ethylbenzene is present in the raffinate 135, additional $C_{9+}$ compounds can also be made. As a result, the $C_{8+}$ isomerate stream 155 can be distilled in distillation column 120 prior to introduction into para-xylene recovery unit 130.

Due to similarities in the boiling points of the various $C_8$ aromatic isomers, distillation is not an effective method for separation of para-xylene from other xylenes and/or ethylbenzene. Instead, para-xylene is typically separated from a $C_8$ aromatic fraction or stream by other convenient methods, such as by selective adsorption or crystallization. U.S. Pat. Nos. 5,750,820 and 8,529,757 (each of which is incorporated herein by reference in its entirety) describe selective adsorption methods which can be referred to as a simulated moving bed. The selective adsorption or crystallization can result in formation of a para-xylene enriched product stream and a para-xylene depleted stream that contains other $C_8$ isomers. The para-xylene depleted stream can be used and/or recycled, for example, as a feed for a xylene isomerization process, which can isomerize at least a portion of the other $C_8$ isomers to form para-xylene. The isomerized product can then undergo further separation to recover additional para-xylene.

Figure 2:
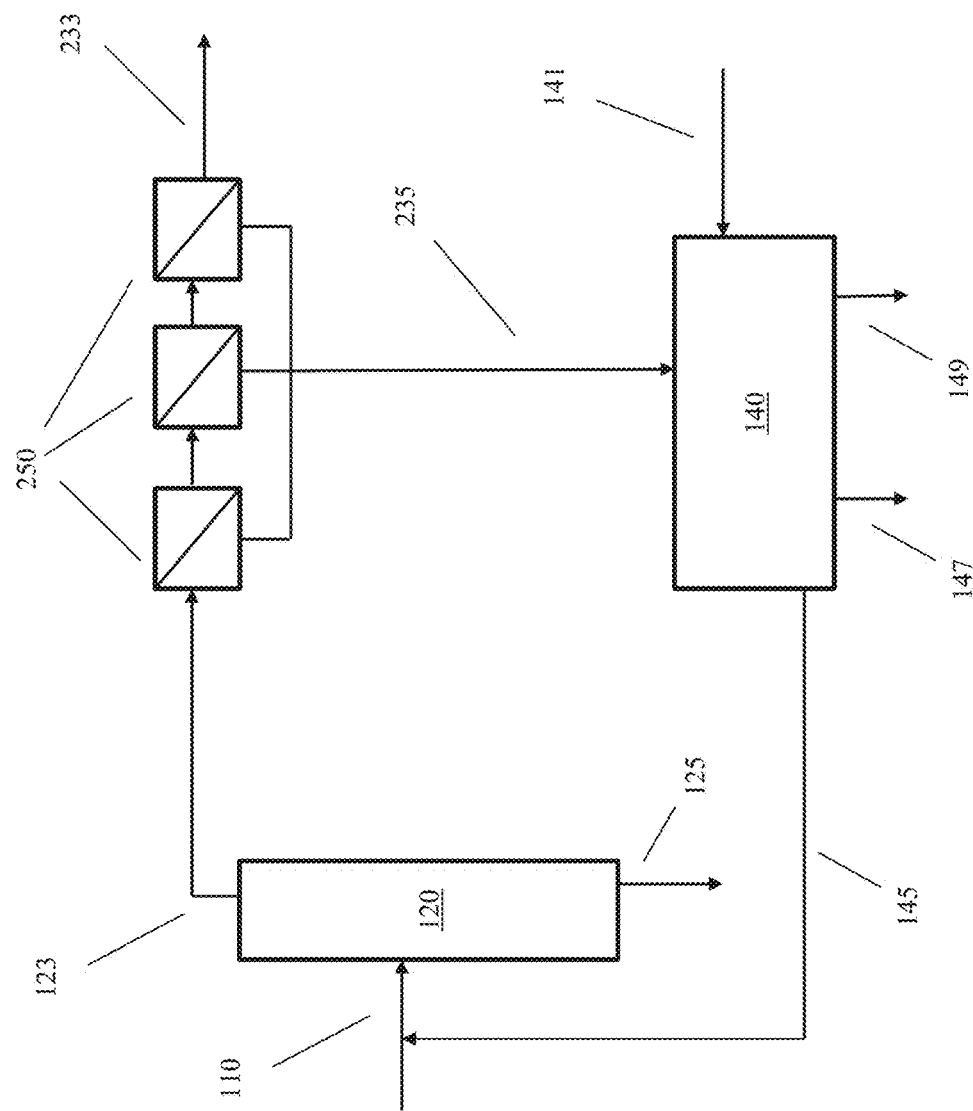
FIG. 2 schematically shows a process configuration including a hydrocarbon reverse osmosis membrane for separation of a stream of higher purity para-xylene from a mixed aromatic input stream.

Use of hydrocarbon reverse osmosis membranes can allow for several types of improvements in a configuration for para-xylene separation. FIG. 2 shows an example of one type of improvement. In FIG. 2, the para-xylene recovery unit 130 from FIG. 1 has been replaced with a series of hydrocarbon reverse osmosis membranes 250. In FIG. 2, the raffinate 235 corresponds to a combined raffinate from the reverse osmosis membranes 250, while the higher purity para-xylene stream 233 corresponds to the permeate from the final reverse osmosis membrane 250. Optionally, a single reverse osmosis membrane 250 can be sufficient for achieving a desired purity for higher purity para-xylene stream 233. The high permeation rates and para-xylene selectivity that can be achieved using hydrocarbon reverse osmosis membranes can allow a membrane separation to provide commercial purification rates and/or can reduce or minimize the number of separation stages or units that needed for purification.

Figure 3:
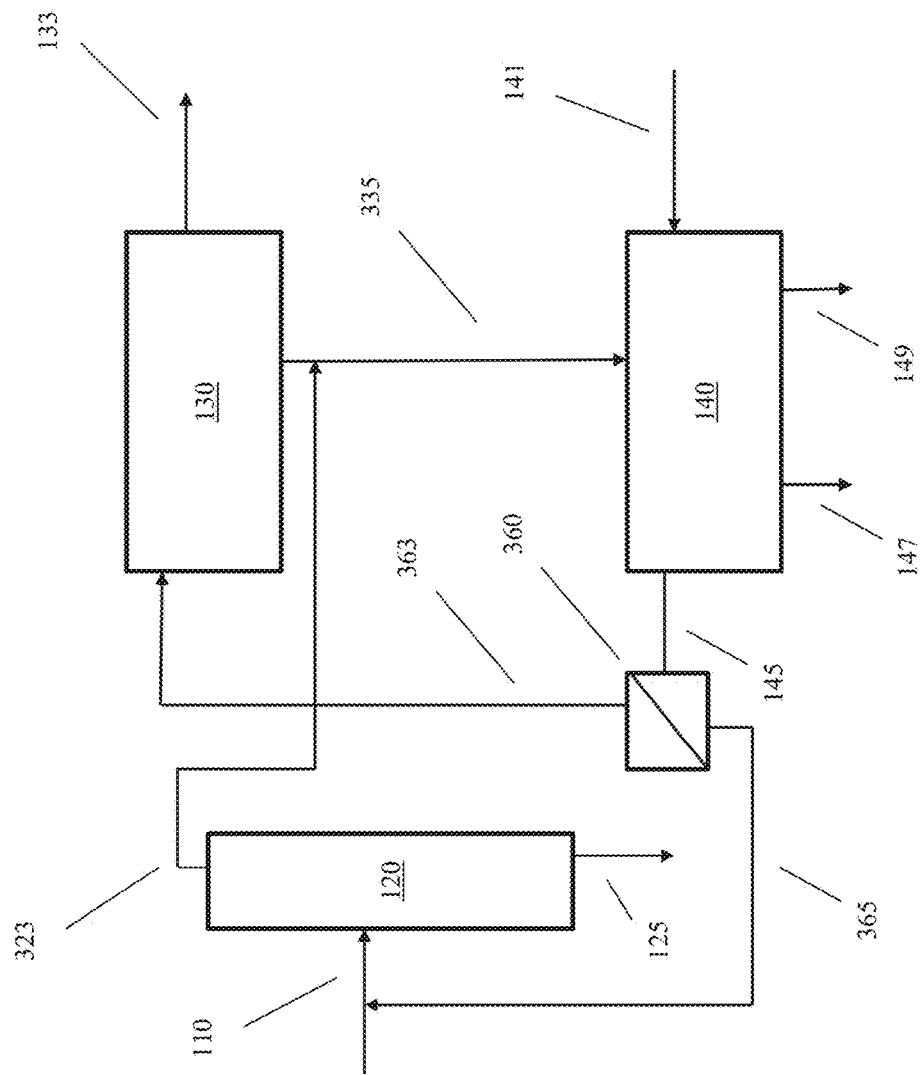
FIG. 3 schematically shows a process configuration including a hydrocarbon reverse osmosis membrane for separation of a stream of higher purity para-xylene from a mixed aromatic input stream.

FIG. 3 shows another variation where a hydrocarbon reverse osmosis membrane 360 is used to separate the $C_{8+}$ isomerate stream 155 generated by isomerization unit 140 and optional additional distillation unit 128. This can allow for production of a para-xylene enriched stream 363 and a para-xylene lean $C_{8+}$ stream 365 that can be returned to the distillation column. In the configuration shown in FIG. 3, the addition of para-xylene lean $C_{8+}$ stream 365 into the input stream 110 results in a combined stream that is lower in para-xylene content. As a result, the $C_8$ stream 323 from distillation column 120 can be introduced into isomerization unit 140 along with raffinate 335. The para-xylene enriched stream 363 from hydrocarbon reverse osmosis membrane 360 is the stream passed into para-xylene recovery unit 130 for formation of a para-xylene enriched product 133.

Figure 4:
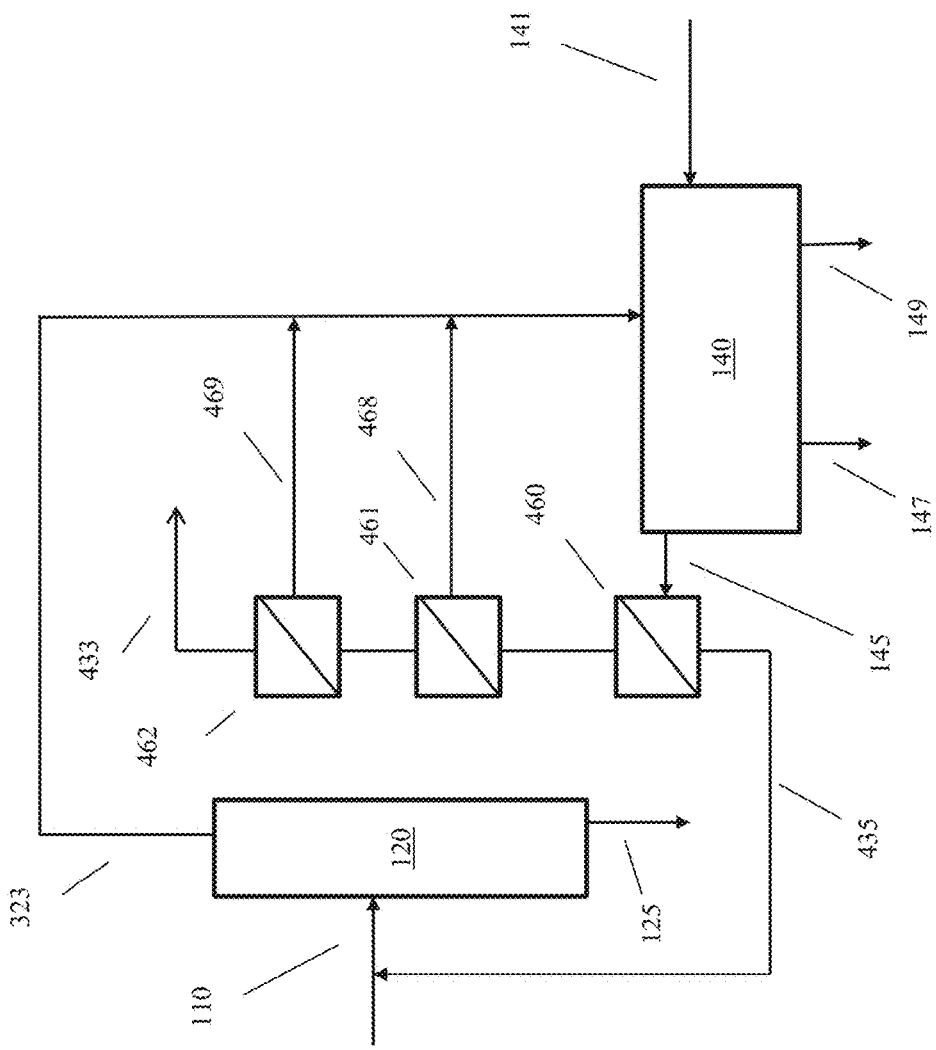
FIG. 4 schematically shows a process configuration including a hydrocarbon reverse osmosis membrane for separation of a stream of higher purity para-xylene from a mixed aromatic input stream.

FIG. 4 shows still another variation where the features of FIGS. 2 and 3 are combined. In FIG. 4, the $C_{8+}$ isomerate stream 155 is passed through a series of hydrocarbon reverse osmosis membranes, such as hydrocarbon reverse osmosis membranes 460, 461, and 462. The use of a plurality of hydrocarbon reverse osmosis membranes can allow for production of a higher purity para-xylene stream 433 while potentially eliminating the need for a separate para-xylene recovery unit. In FIG. 4, the retentate streams 468 and 469 from reverse osmosis membranes 461 and 462 are returned to the isomerization unit 140 along with the $C_8$ stream 323 from distillation column 120. The retentate 435 from reverse osmosis membrane 460 is returned to the distillation column 120.

Typically xylene streams found in chemical or petrochemical plants also contain ethylbenzene. Ethylbenzene can pose difficulties in conventional xylene isomerization and separation systems, as ethylbenzene has a similar boiling point to other xylene isomers. Thus, attempting to separate ethylbenzene from xylenes by distillation can lead to reduced yields from a xylene isomerization and separation process. Conventional isomerization technologies operating at high temperatures (e.g.: 400° C.) in vapor phase isomerize the xylenes and dealkylate ethylbenzene to benzene. Although vapore phase isomerization has lower efficiency and/or throughput than liquid phase isomerization, conventional liquid phase isomerization processes can have difficulty in removing and/or converting ethylbenzene. This can lead to accumulation of ethylbenzene in a liquid isomerization system. The cracking provided during vapor phase isomerization can reduce or minimize such accumulation.

U.S. Pat. No. 8,697,929 describes an example of a liquid phase isomerization system, the entirety of which is incorporated herein by reference. Briefly, liquid phase isomerization of xylenes can be performed at a temperature of less than 295° C. and a pressure sufficient to maintain the xylenes in liquid phase. In embodiments, the process utilizes a catalyst comprising a zeolite, preferably at least one selected from the group consisting of ZSM-5 and MCM-49. In embodiments, the process utilizes a catalyst comprising ZSM-5 along with a binder or the ZSM-5 may be self-bound. Optionally, the catalyst can be characterized by one or more of the following characteristics: the ZSM-5 is in the proton form (HZSM-5); the ZSM-5 has a crystal size of less than 0.1 microns; the ZSM-5 has a mesoporous surface area (MSA) greater than 45 m²/g; the ZSM-5 has a zeolite surface area (ZSA) to mesoporous surface area (MSA) ratio of less than 9; a silica to alumina weight ratio in the range of 20 to 50. The reactor(s) containing the isomerization catalyst can include at least one bed of catalyst, such as a fixed bed of catalyst. The reactor can be operated as a downflow reactor, an upflow reactor, or in another convenient manner.

A conventional liquid phase isomerization process comprises contacting a feedstream comprising $C_8$ aromatic hydrocarbons with a catalyst suitable for isomerization at a temperature below 295° C., preferably below 280° C., and at a pressure sufficiently to keep the reactant in liquid phase. One of skill in the art would be able to determine other operating characteristics, such as a lower temperature, within which the present invention may be practice. Lower limits may be, for instance, above 180° C. or 190° C. or 200° C., or 210° C., and the like. The flow rate can be selected by one of ordinary skill in the art in possession of the present disclosure, but may advantageously be selected within the range from 0.1 to 100 hr$^{-1}$ WHSV, preferably from 0.5 to 20 hr$^{-1}$ WHSV, and more preferably from 1 to 10 hr$^{-1}$ WHSV.

Additional Xylene Isomerization and Separation Configurations

Figure 22:
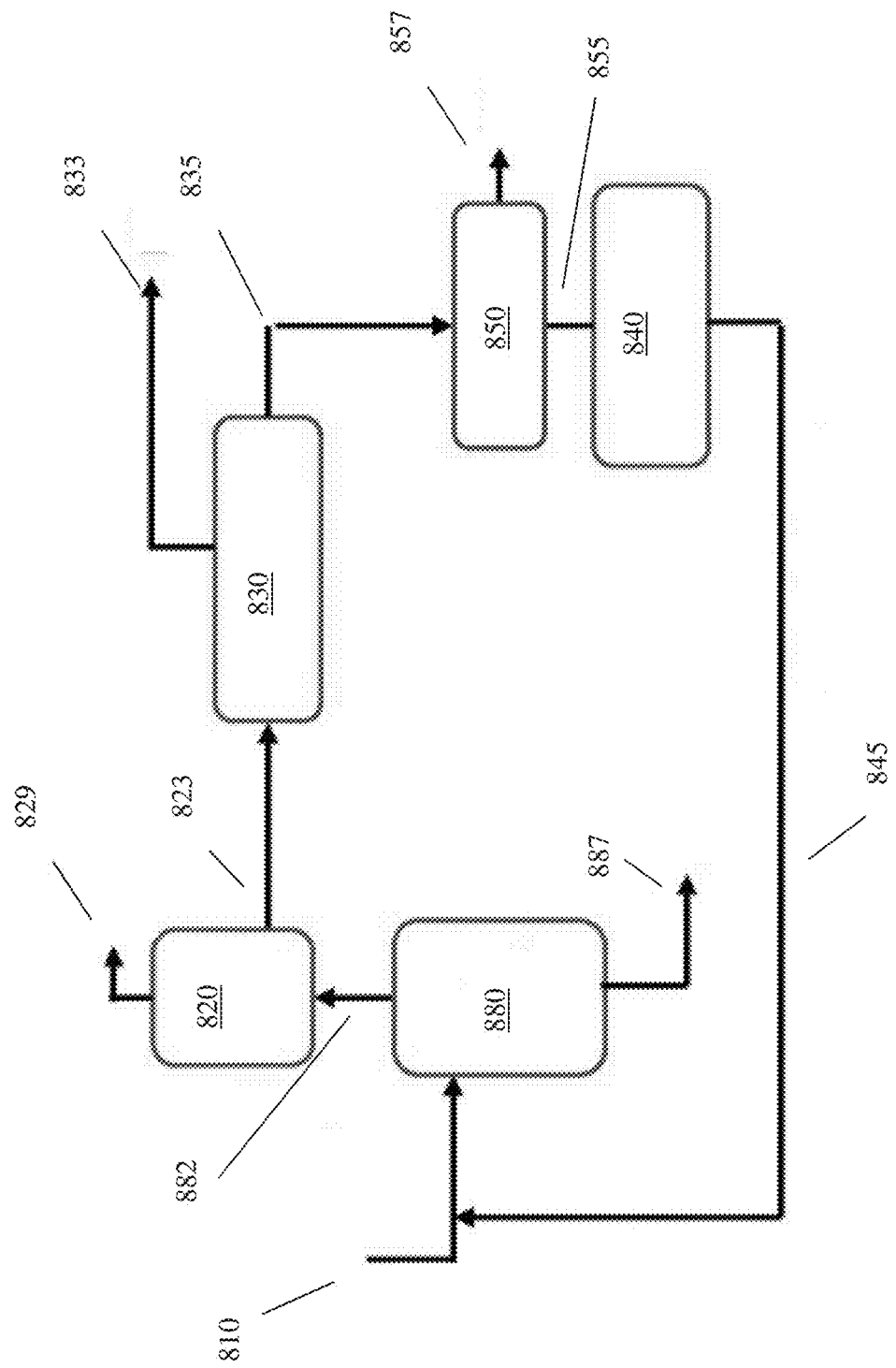
FIG. 22 schematically shows a process configuration including a hydrocarbon reverse osmosis membrane for separation of a stream of higher purity para-xylene from a mixed aromatic input stream.

FIG. 22 provides another example of a xylene loop configuration that can be used in conjunction with a selective membrane. In FIG. 22, xylene-containing feed 810 can be introduced into distillation column 880 or another type of fractionator/separator. Distillation column 880 can generate a lower boiling fraction 882 and a bottoms fraction 887. Bottoms fraction 887 can be enriched in, for example, $C_{9+}$ compounds from feed 810. Lower boiling fraction 882 can be enriched in, for example, one or more of para-xylene, ortho-xylene, meta-xylene, ethylbenzene, and $C_{7-}$ compounds from feed 810. The lower boiling fraction 882 can then be passed into fractionator 820 to form a light fraction 829 comprising $C_{7-}$ compounds and a xylene-enriched stream 823. It is noted that the combination of distillation column 880 and fractionator 820 can be viewed as a single separation stage that comprises a plurality of separators for performing separations based on boiling range. At this point, the xylene-enriched stream 823 can still contain a substantial portion of meta-xylene and/or ortho-xylene, so para-xylene recovery unit 830 can preferably correspond to a simulated moving bed type of recovery unit. Para-xylene recovery unit 830 can generate a para-xylene product stream 833 and a residual stream 835. The residual stream 835 can be passed through a selective membrane 850 to produce a permeate 857 enriched in ethylbenzene and a retentate 855 enriched in meta-xylene. The retentate 855 can then be passed into a liquid phase isomerization reactor 840. The isomerized effluent 845 from liquid phase isomerization reactor 840 can then be used as additional feed 810 to the distillation column 880.

Example—Characterization of PVDF Hollow Fiber Membrane Structures

Hollow fiber asymmetric membrane structures were formed by using a co-annular spinneret with two types of PVDF solutions as described above. Polymer solutions comprising solvent, non-solvent, and polymer were prepared. For the core polymer solution, dimethylacetamide (DMAc) was used as a solvent and mixture of lithium chloride (LiCl) and water were used as non-solvents. For the sheath polymer solution, a mixture of dimethylacetamide and tetrahydrofuran were used as solvents and ethanol was used as a non-solvent. For both core and sheath polymer solutions, poly(vinylidene) fluoride was used as a polymer source. Asymmetric double layer hollow fibers were created via nonsolvent phase inversion technique. The aforementioned polymer solutions were extruded through a spinneret into a non-solvent quench bath and further taken-up on a spinning drum at desired speed.

After formation of hollow fiber structures, some hollow fiber structures were pyrolyzed without prior cross-linking. Other hollow fiber structures were exposed to cross-linking and then pyrolyzed.

Figure 5:
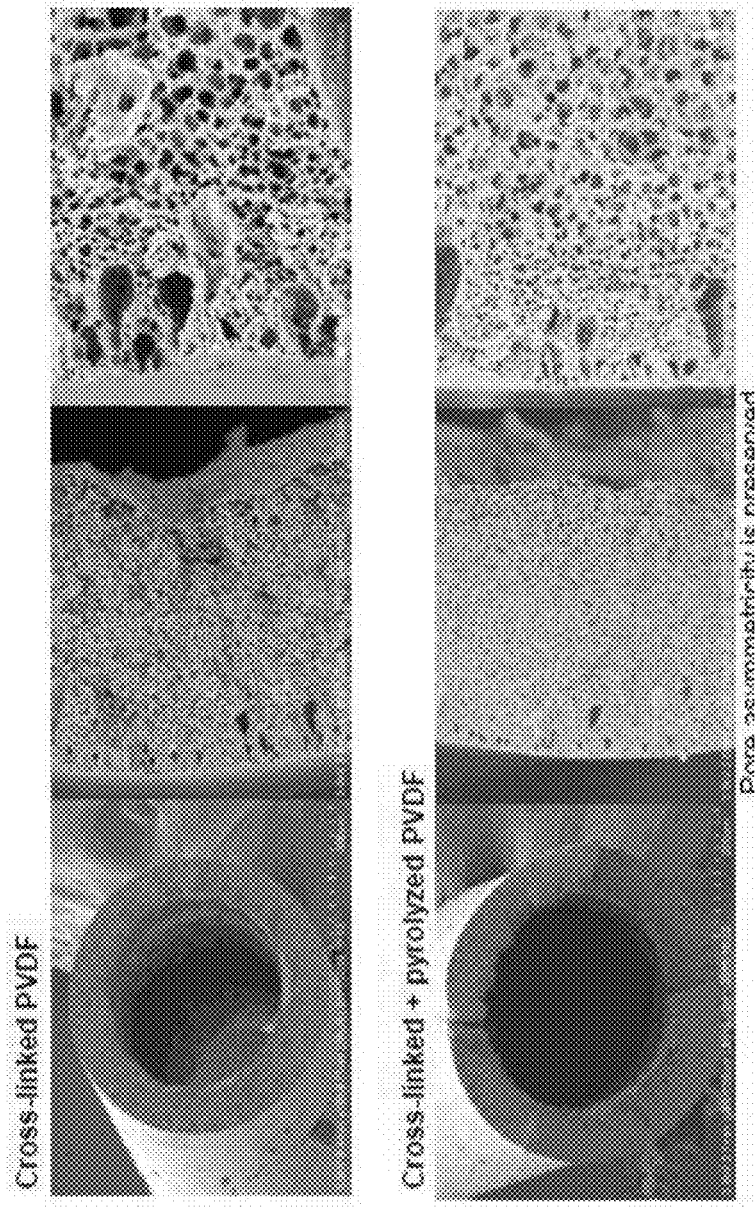
FIG. 5 shows examples of asymmetric membrane structures.

FIG. 5 shows SEM micrographs of hollow fiber structures that were either cross-linked (top series) or cross-linked and then pyrolyzed at 550° C. in an argon atmosphere (bottom series).

As shown in FIG. 5, the porous nature of the core portion of the hollow fiber structure is retained in the final hollow fiber membrane structure after pyrolysis. This allows the asymmetric structure (dense sheath, porous core) original present in the hollow fiber structure to be preserved after pyrolysis is used to form the hollow fiber membrane structure.

Figure 6:
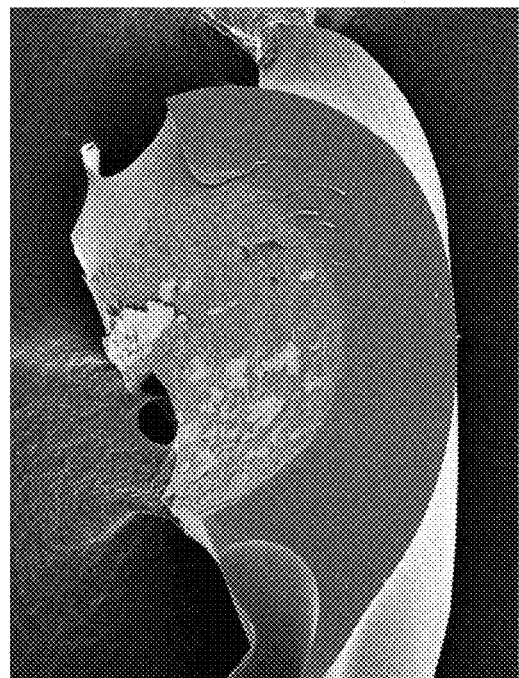
FIG. 6 shows examples of a membrane structure formed from non-cross-linked polyvinylidene fluoride before and after pyrolysis.
Figure 6:
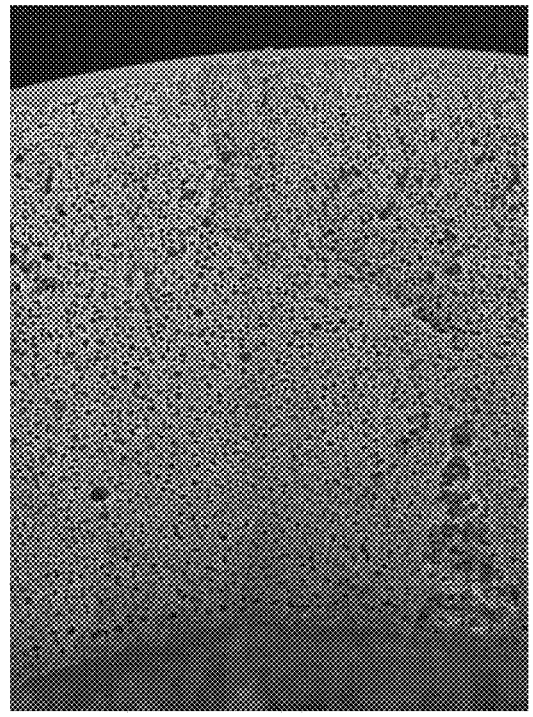

The preserved asymmetric membrane structure shown in FIG. 5 is in contrast to the structure shown in the SEM micrographs in FIG. 6, which shows a hollow fiber structure before and after pyrolysis when cross-linking is not used. In the left micrograph, the hollow fiber structure is shown prior to pyrolysis. The difference in porosity between the outer sheath layer and the porous core is visible in the micrograph. The right micrograph shows the structure after pyrolysis. Because cross-linking was not performed, the pore structure in the core has collapsed, resulting in a symmetric dense structure throughout.

Figure 16:
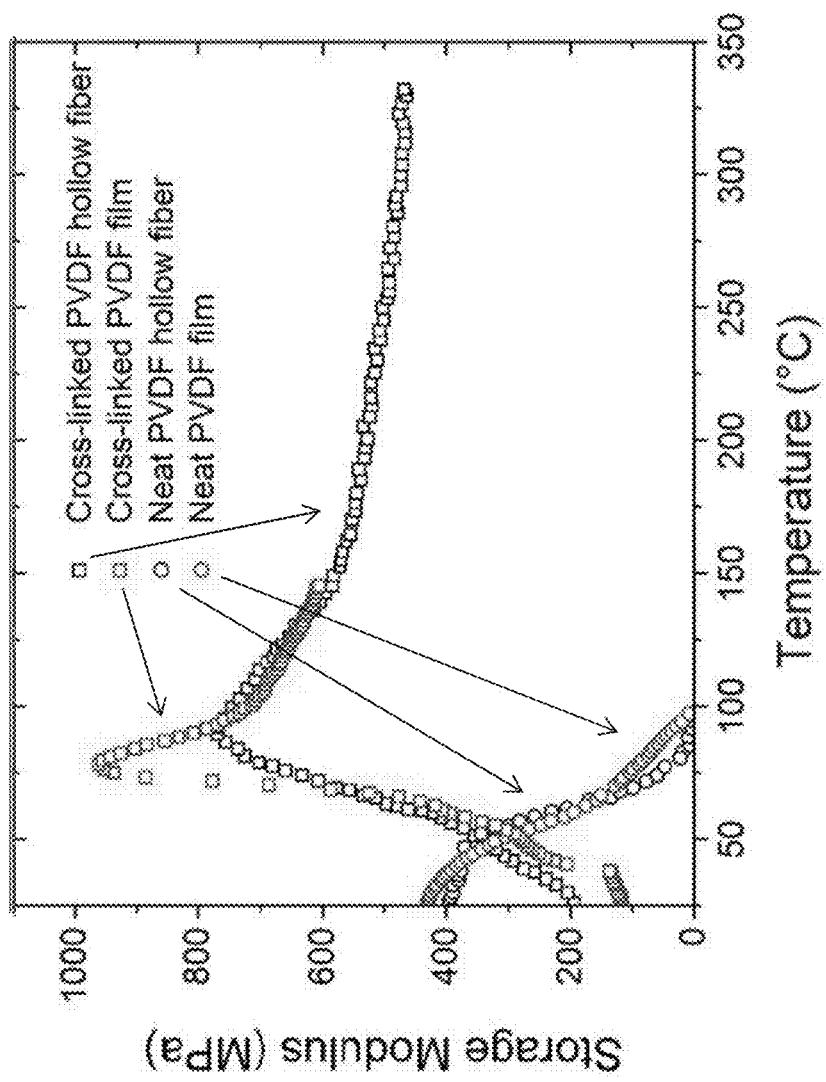
FIG. 16 shows storage modulus values for polyvinylidene fluoride membrane structures with and without cross-linking.

FIG. 16 provides additional details regarding the impact of cross-linking the PVDF structure prior to pyrolysis. FIG. 16 shows the structural modulus of flat and hollow fiber structures during a pyrolysis process for both cross-linked and non-cross-linked structures. As shown in FIG. 16, the PVDF structures that were not cross-linked prior to pyrolysis actually have a higher initial structural modulus value. However, heating the non-cross-linked structures quickly reduces the structural modulus, until the structural modulus reaches zero at a temperature of about 100° C. At a structural modulus of zero, the PVDF structure acquires fluid-like properties. This loss of structural modulus is believed to correspond with the loss of porosity for the core when cross-linking is not performed prior to pyrolysis. By contrast, the cross-linked structures achieve a maximum structural modulus at temperatures near 100° C. Further heating of the cross-linked structures results in structural modulus values that asymptotically approach about 500 MPa.

Figure 7:
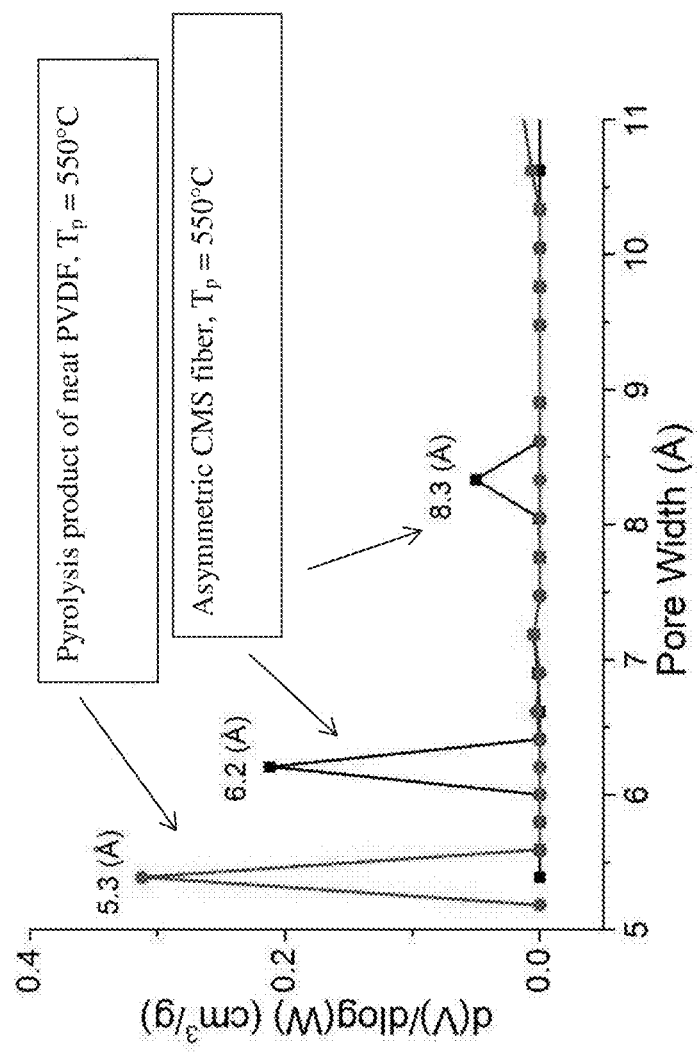
FIG. 7 schematically shows examples of pore size distributions for porous carbon membrane structures formed by pyrolysis of polyvinylidene fluoride membrane structures with and without prior cross-linking.

The use of cross-linking prior to pyrolysis also impacts the nature of the amorphous pore structure formed in the sheath layer. FIG. 7 shows the pore size distribution (alternatively referred to here as pore width) for the sheath layer after pyrolysis for hollow fiber membrane structures formed with and without cross-linking. The pore size distribution in FIG. 7 was derived from nitrogen physisorption (BET). As shown in FIG. 7, when pyrolysis was performed on the PVDF hollow fiber structure without prior cross-linking, the resulting sheath layer had a unimodal pore size distribution with a median size of about 5.2 Angstroms. When pyrolysis was performed after cross-linking, the resulting sheath layer had a bimodal pore distribution, with median pore sizes of 6.3 Angstroms and 8.2 Angstroms. Thus, cross-linking of the hollow fiber structure provides multiple benefits. In addition to maintaining the asymmetric nature of the structure after pyrolysis as shown in FIG. 5, performing cross-linking prior to pyrolysis also increases the median pore size for the smallest pore size peak in the pore size distribution.

Figure 8:
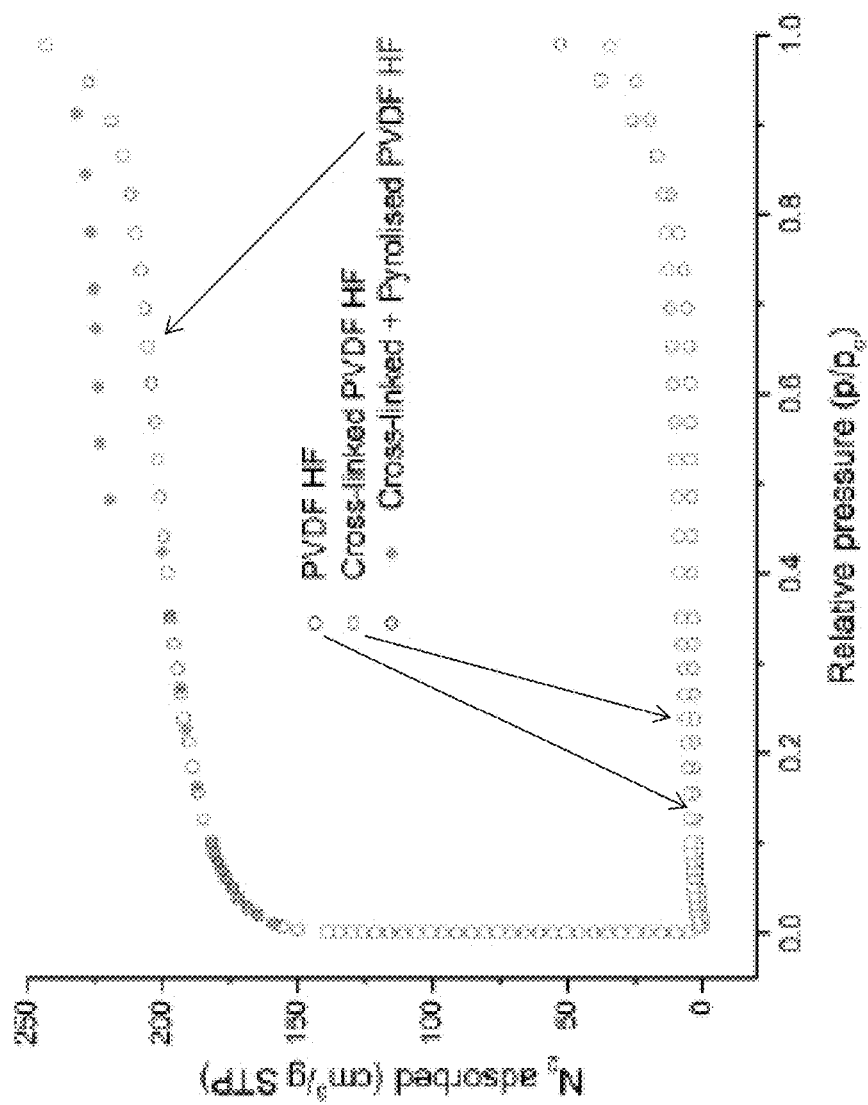
FIG. 8 shows examples of $N_2$ physisorption on polyvinylidene fluoride and porous carbon membrane structures.

FIG. 8 shows nitrogen physisorption data for the sheath layer of a hollow fiber structure as formed, the structure after cross-linking, and the structure after cross-linking and pyrolysis. As shown in FIG. 8, the sheath layer has a minimal surface area when initially formed. Cross-linking may slightly increase the surface area, but otherwise the surface area of the cross-linked surface appears to be similar to the surface area of the surface when initially formed. Based on the surface area values of less than 50 $cm^2/g$, both the sheath as formed and the sheath after cross-linking have a minimal amount of pore structure. By contrast, after cross-linking and pyrolysis the sheath layer has a surface area of greater than 700 $cm^2/g$. This indicates the pyrolysis causes formation of a substantial pore structure.

Figure 9:
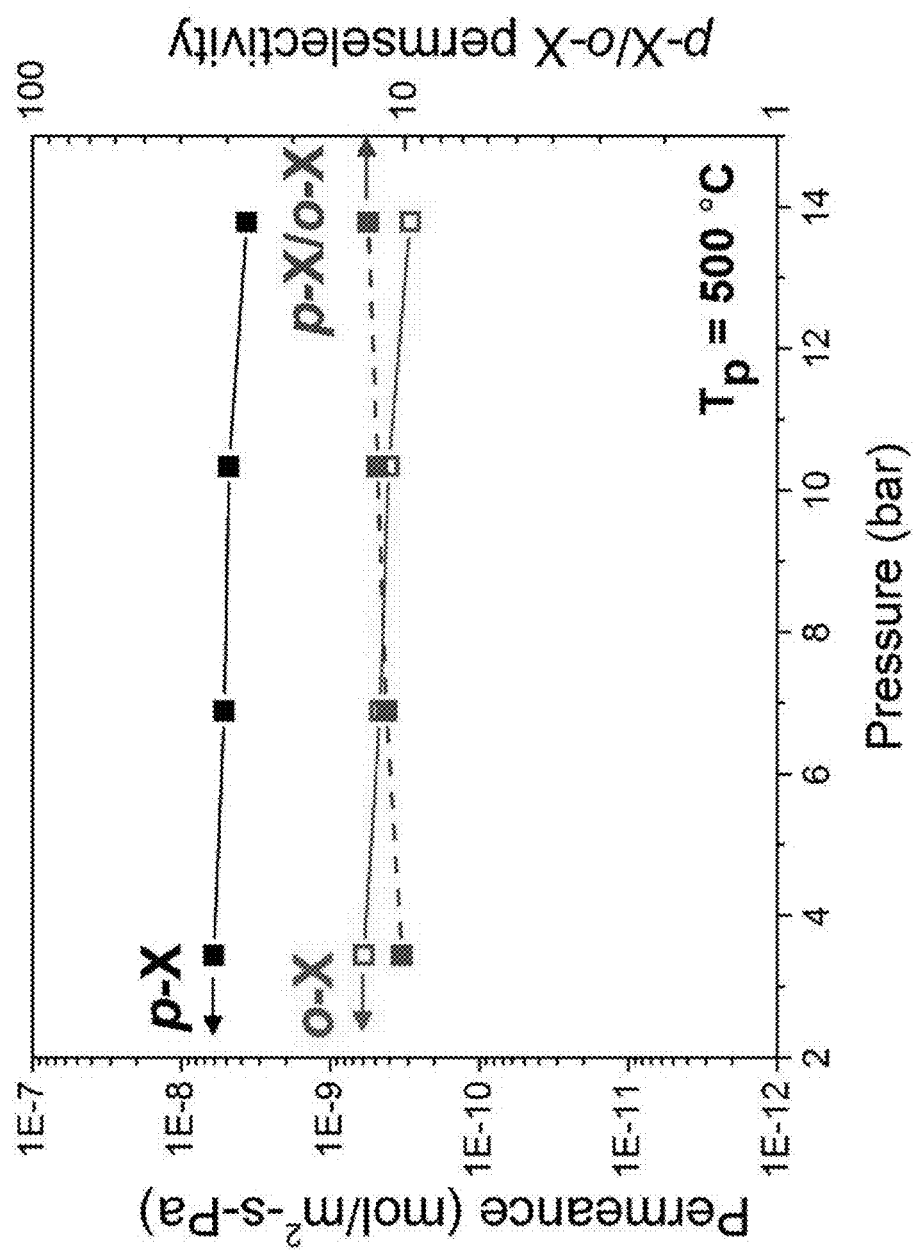
FIG. 9 shows single component permeance values for various single ring aromatic compounds with respect to an asymmetric porous carbon membrane structure.
Figure 10:
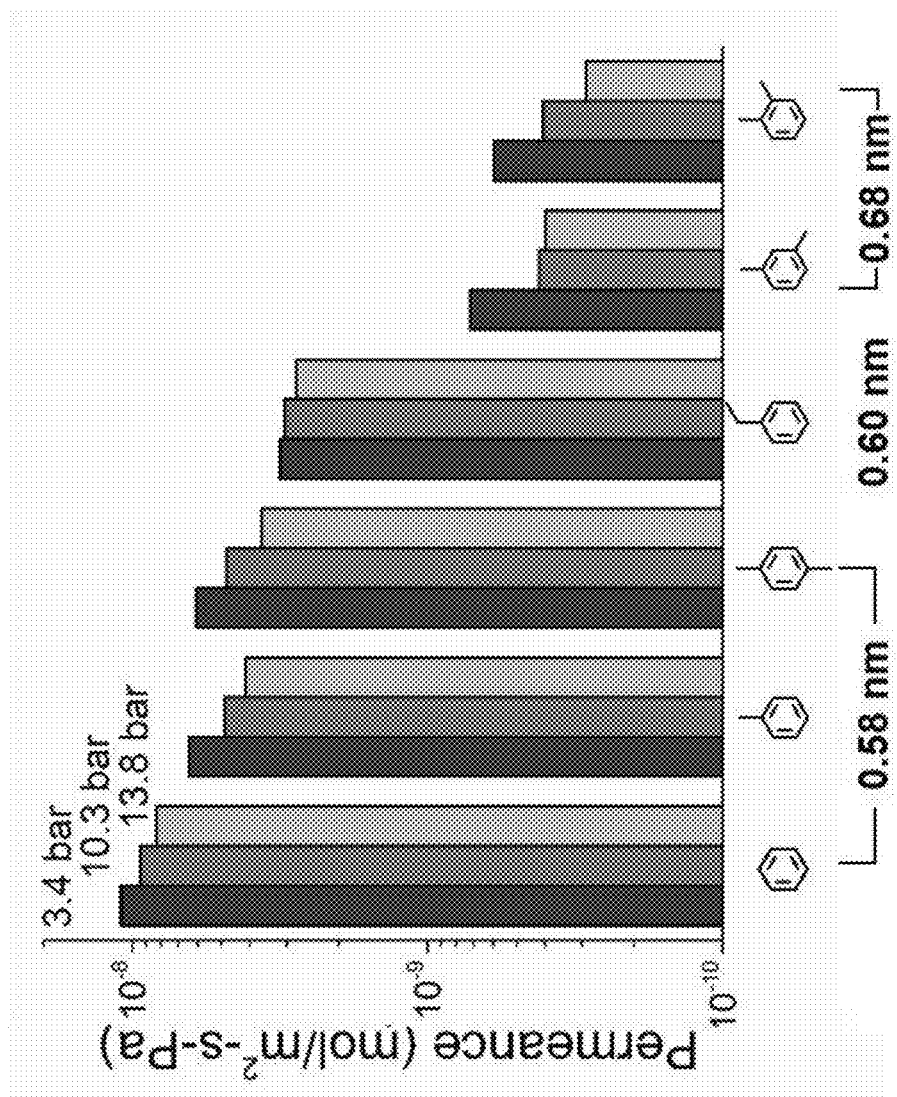
FIG. 10 shows single component permeance values for various single ring aromatic compounds with respect to an asymmetric porous carbon membrane structure.

The substantial pore network formed after cross-linking and pyrolysis of the PVDF hollow fiber structure can be used for hydrocarbon reverse osmosis separation of molecules. Suitable molecules for separation can have appropriate sizes relative to the 6.2 Angstrom smallest median pore size of the pore network. FIG. 9 shows an example of single compound permeance (left vertical axis) for para-xylene (5.8 Angstroms) and ortho-xylene (6.8 Angstroms) as a function of pressure. FIG. 9 also shows the expected relative selectivity (right axis) based on the single compound permeance values. As shown in FIG. 9, the expected or ideal selectivity increases as the feed pressure to the membrane increases. FIG. 10 shows permeance values for the various xylene isomers, as well as for the additional compounds benzene, toluene, and ethylbenzene, at 340 kPa-a, 1030 kPa-a, and 1380 kPa-a. As shown in FIG. 10, para-xylene has comparable permeance values to toluene (and somewhat comparable to ethylbenzene). This is in contrast to the higher permeance values for benzene and the lower permeance values for meta-xylene and ortho-xylene.

Figure 11:
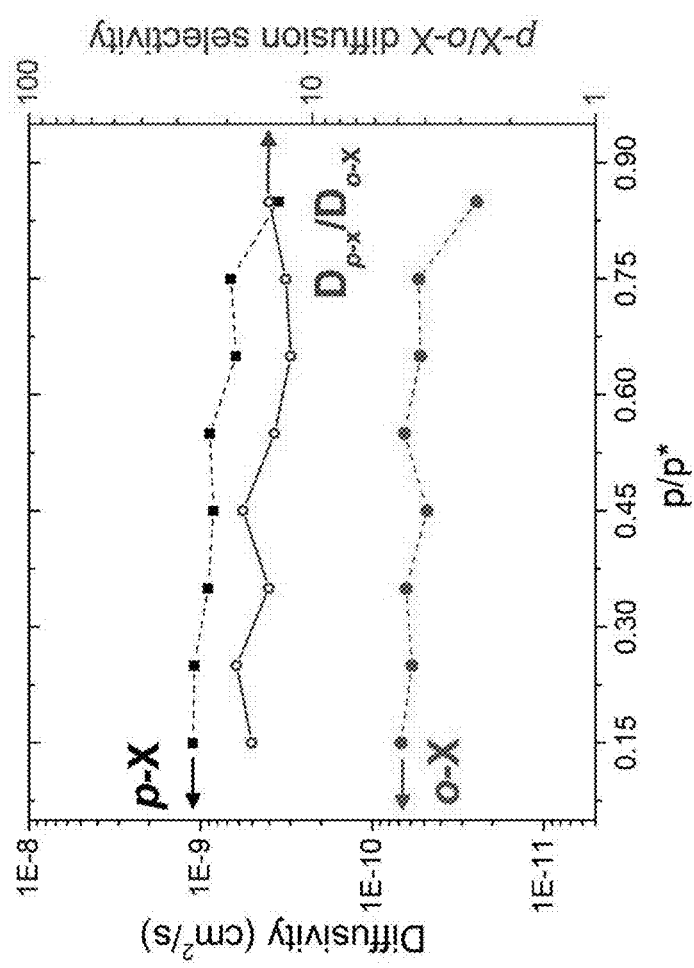
FIG. 11 shows diffusivity values for para-xylene and ortho-xylene with respect to an asymmetric porous carbon membrane structure.
Figure 12:
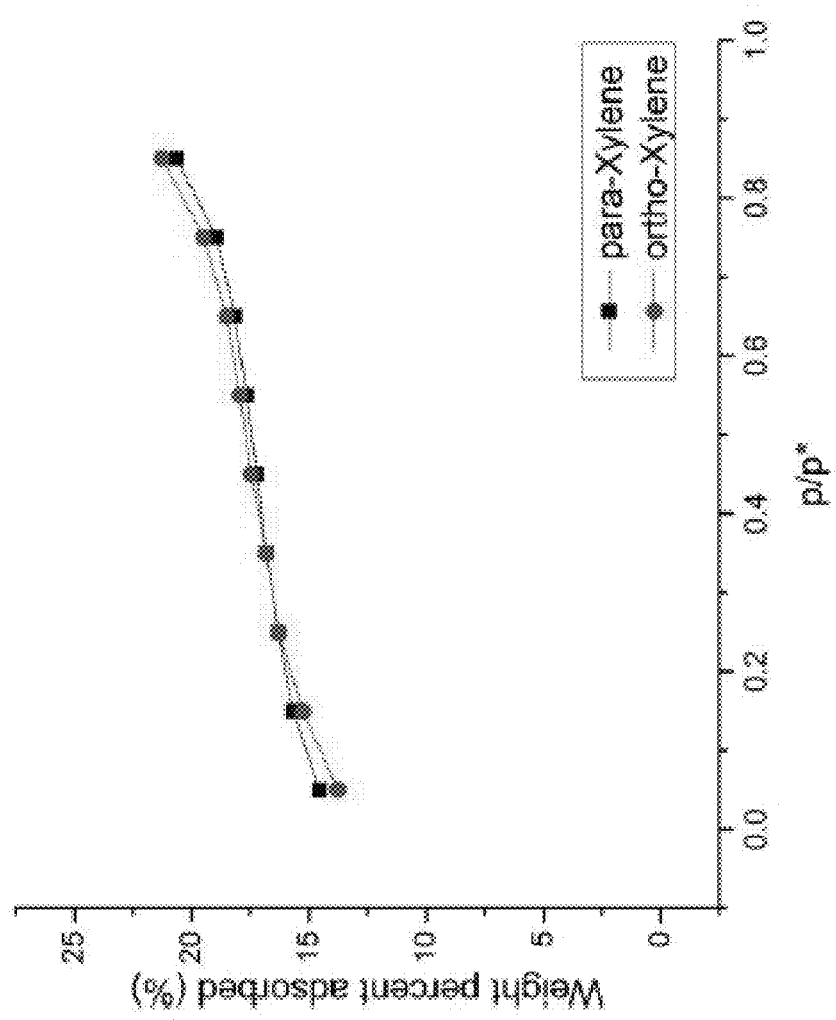
FIG. 12 shows adsorption as a function of pressure for para-xylene and ortho-xylene with respect to an asymmetric porous carbon membrane structure.

FIG. 11 shows the diffusivity of para-xylene and ortho-xylene based on the partial pressure of the component in the feed to the membrane. The diffusivity values in FIG. 11 were calculated based on real time uptake in a membrane sample. The membrane material was placed in a quartz pan attached to a microbalance. The weight of the sample was measured once per minute as the sample was exposed to different relative pressures of xylene in a flowing nitrogen stream. FIG. 11 also shows the ratio of the diffusivity values. As shown in FIG. 11, the diffusivity for para-xylene is about an order of magnitude greater than the diffusivity of ortho-xylene under similar conditions. FIG. 12 shows that the weight percent adsorbed for para-xylene and ortho-xylene as a function of pressure is similar. Instead of being based on solvation, the difference in diffusivity between para-xylene and ortho-xylene is based on the ability of the respective compounds to traverse the sheath layer via the pore network.

Figure 13:
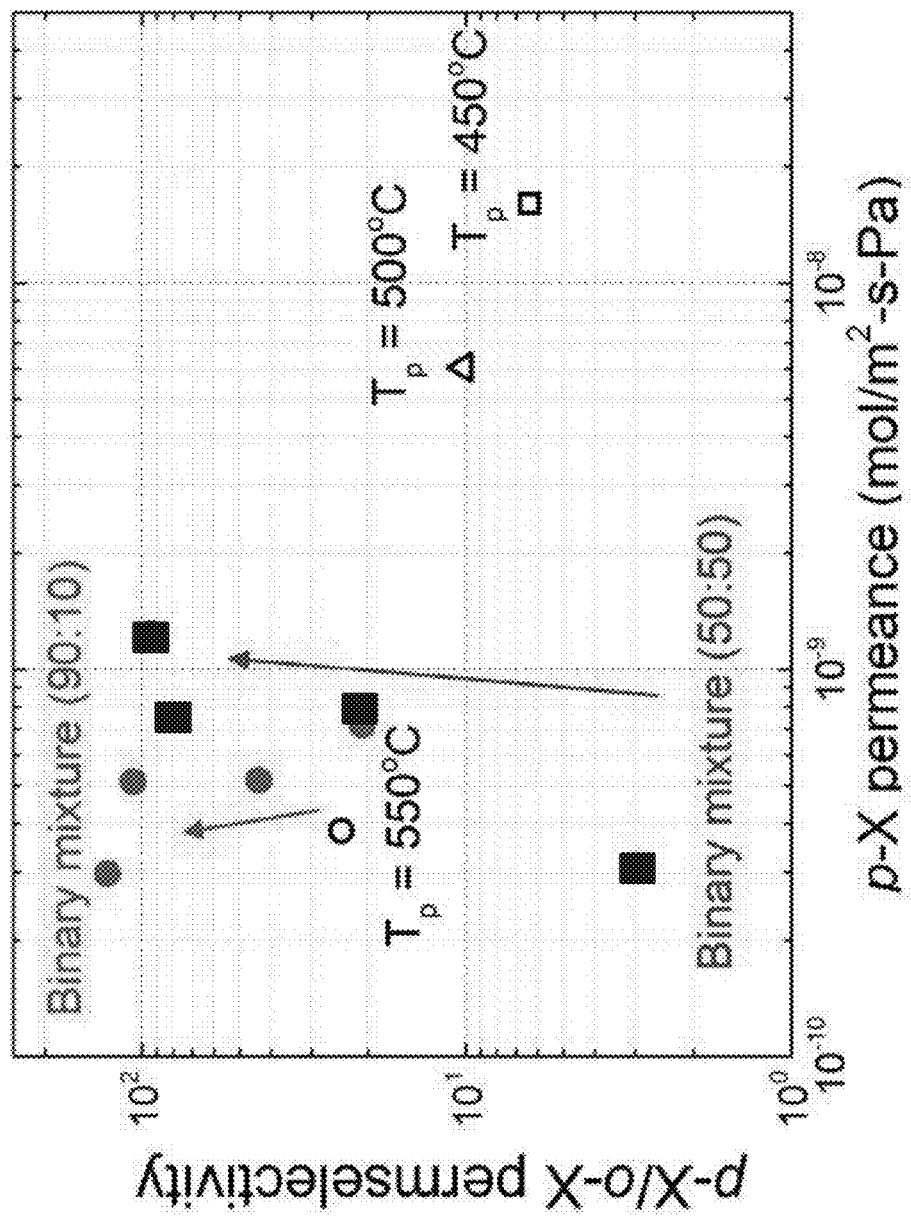
FIG. 13 shows results from hydrocarbon reverse osmosis separation of 50:50 and 90:10 mixtures of para-xylene and ortho-xylene.

FIGS. 9 and 10 shows single component fluxes and ideal selectivities for membrane structures formed after pyrolysis at 550° C. FIG. 13 shows how the ideal selectivities of the membrane structure change based on changes in the pyrolysis temperature. In FIG. 13, the open symbols correspond to ideal selectivities as a function of p-xylene permeance at 450° C., 500° C., and 550° C. The solid symbols correspond to measured values either for a 50/50 composition or a 90/10 composition of p-xylene and o-xylene. As shown in FIG. 13, increasing the pyrolysis target temperature causes an increase in the selectivity for separation of para-xylene and ortho-xylene. Without being bound by a particular theory, this is believed to be due to a narrowing of the peaks in the pore size distribution. This can lead to an overall reduced rate of flow across the sheath layer, but can allow for increased selectivity for permeation of para-xylene across the sheath layer. It is also noted that the measured multi-component selectivities in FIG. 13 are higher than the predicted selectivities based single component values. This is a surprising result, as for some types of membranes, multi-component selectivites can tend to be lower than predicted selectivities based on single component measurements.

Figure 14:
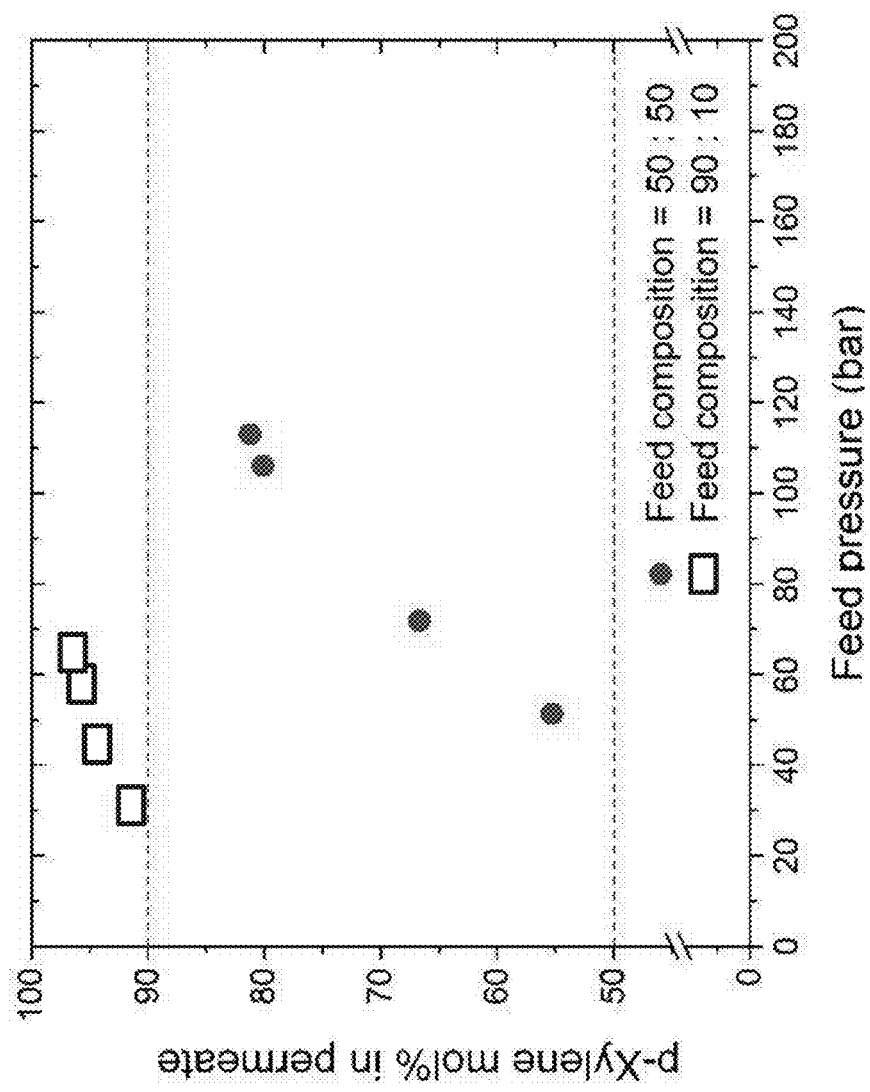
FIG. 14 shows results from hydrocarbon reverse osmosis separation of 50:50 and 90:10 mixtures of para-xylene and ortho-xylene.

FIG. 14 shows the resulting para-xylene content in the permeate for the measured data points shown in FIG. 13. As shown in FIG. 14, the membrane was effective for forming a permeate with increased para-xylene concentration. As the feed pressure was increased, the para-xylene concentration in the permeate also increased. For the 90/10 ratio feed, at higher pressures a para-xylene permeate was formed that approached 99 wt % in purity.

Figure 15:
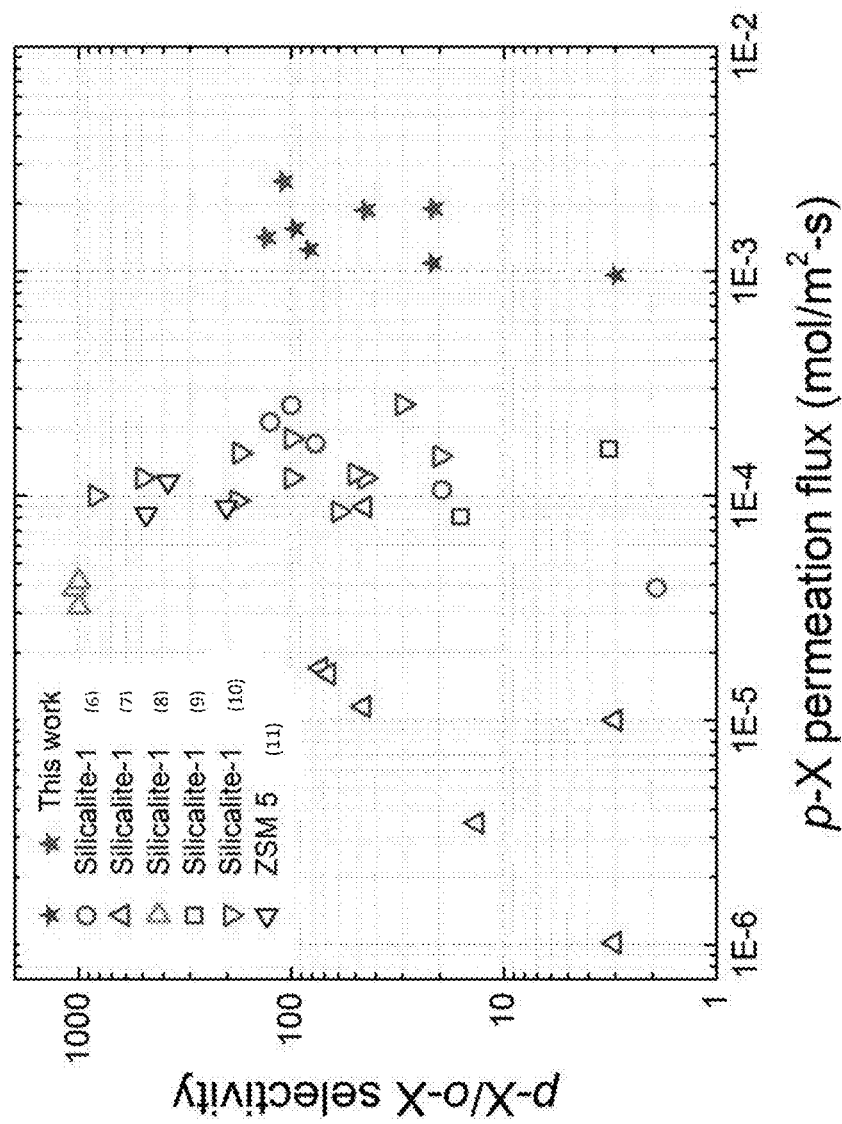
FIG. 15 shows results from hydrocarbon reverse osmosis separation of 50:50 and 90:10 mixtures of para-xylene and ortho-xylene.

FIG. 15 provides a comparison of selectivity for para-xylene in the permeate relative to the total flux across a membrane structure for the data points shown in FIG. 13. In FIG. 15, selectivities relative to permeate flux for a variety of conventional crystalline molecular sieves of MFI framework type are also shown. As noted above, crystalline pore structures may not be suitable for use in the liquid phase conditions corresponding to hydrocarbon reverse osmosis. Instead, crystalline membranes require gas phase separation conditions. This results in a lower permeation rate across the membrane, as shown in FIG. 15. Because hydrocarbon reverse osmosis is performed under liquid phase conditions, the permeation rate is roughly an order of magnitude higher than permeation under gas phase conditions for the conventional MFI framework type molecular sieves shown in FIG. 15.

Example—Membrane Structure Including Porous Metal Structure

Figure 17:
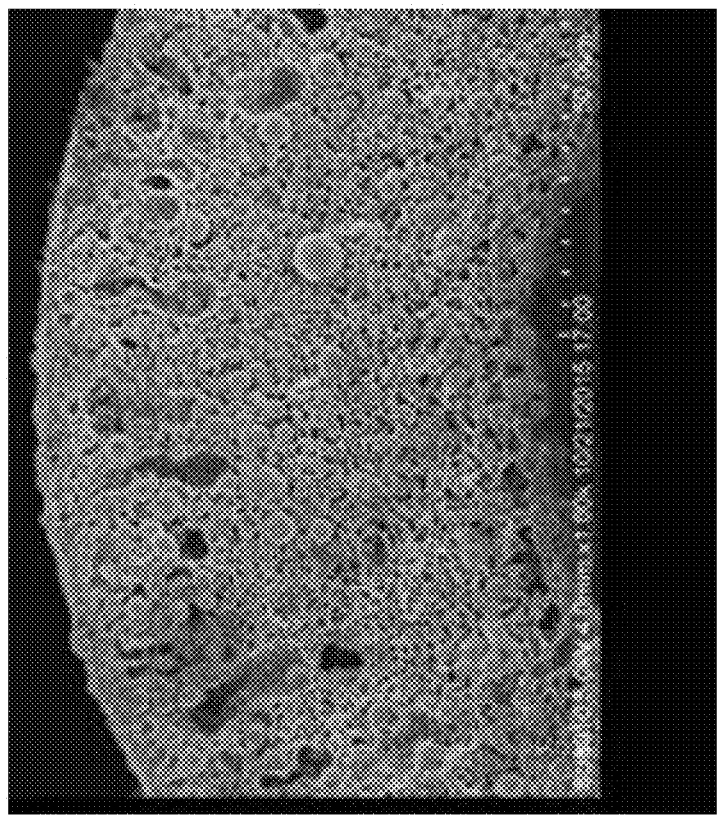
FIG. 17 shows an example of an extruded structure formed from extrusion of a mixture of metal particles and a polymer binder.
Figure 18:
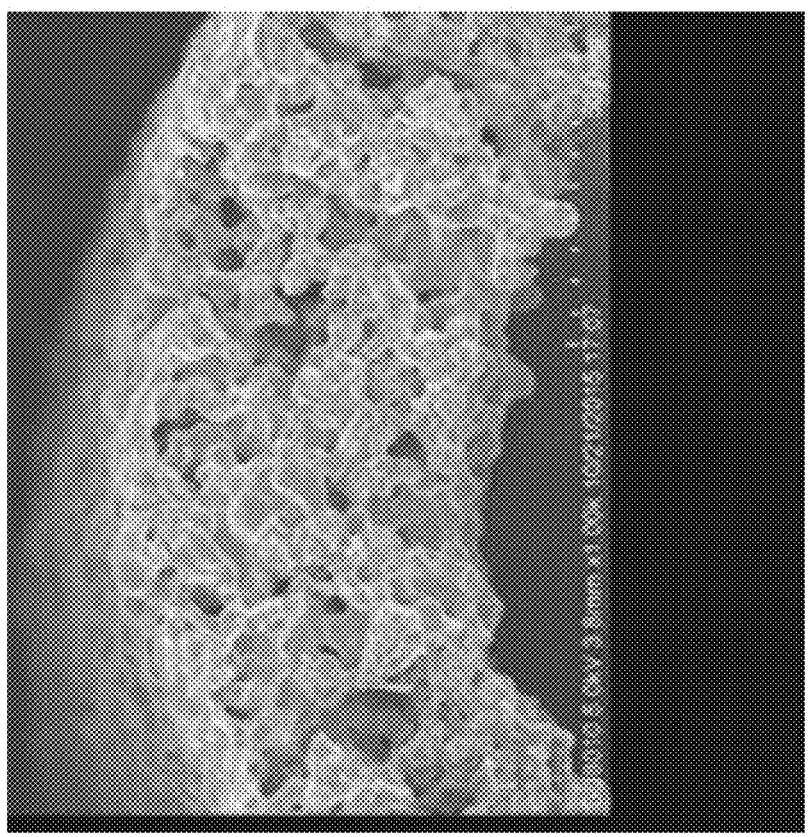
FIG. 18 shows a porous metal structure formed by sintering of the extruded structure of FIG. 17.
Figure 19:
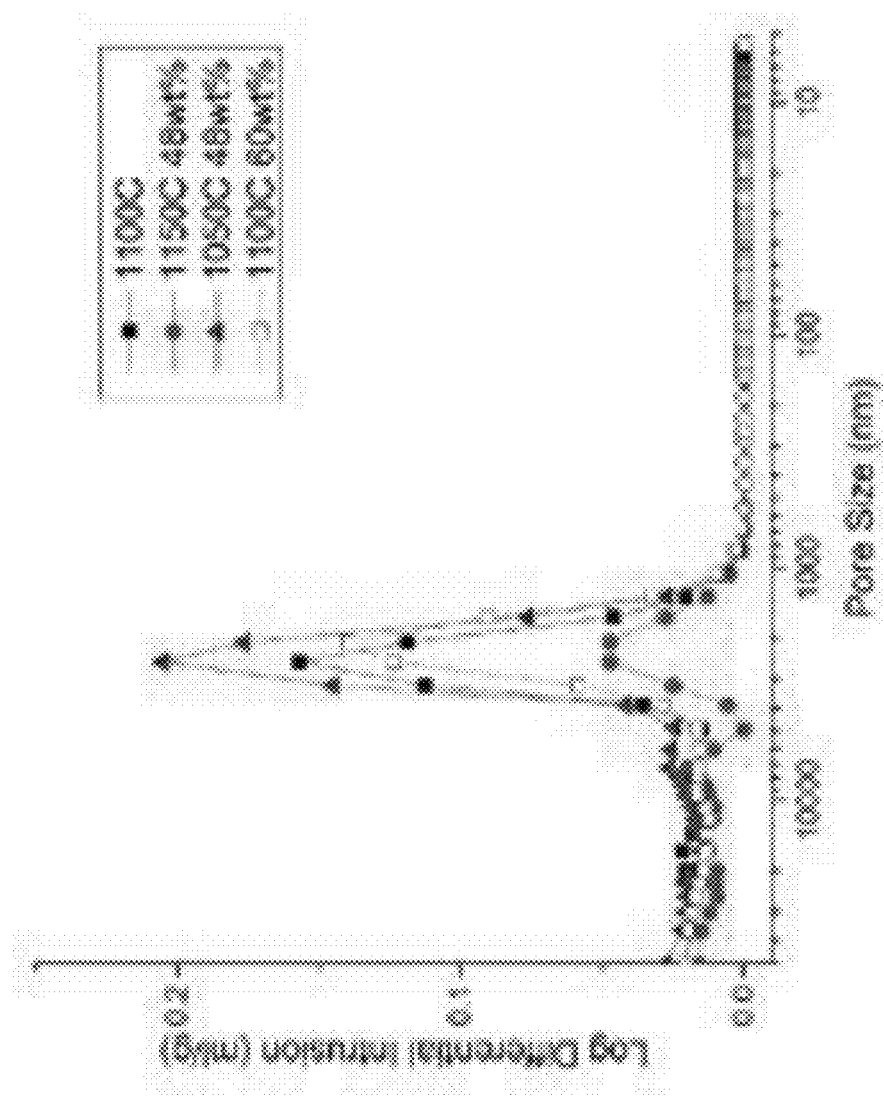
FIG. 19 shows pore size distributions for porous metal structures.

FIG. 17 shows an example of a single layer hollow fiber structure formed from an extrusion mixture of stainless steel particles and PVDF. The stainless steel particles were roughly spherical particles composed of SS316L stainless steel. The particles had an average diameter (characteristic length) of about 3.0 μm. The mixture of stainless steel particles and PVDF was extruded to form an extruded hollow fiber structure having an outer diameter of about 320 μm and an inner diameter of about 215 μm. This roughly corresponds to a thickness of about 53 μm. The extruded hollow fiber structure was then sintered according to a temperature program. After increasing the temperature of the extruded hollow fiber structure to 1100° C. over the course of about 7-8 hours, the extruded hollow fiber structure was sintered at a temperature of about 1100° C. for about 1 hour to form a porous metal membrane structure, as shown in FIG. 18. The length of the sintering process was selected to allow for partial sintering of the metal particles to form the porous metal membrane structure. FIG. 19 shows the pore size distribution for porous metal structures formed according to the above procedure using various sintering temperatures and various mixtures (by weight) of stainless steel metal particles and polymer binder. The weight percentages shown in FIG. 19 correspond to the weight percent of the stainless steel metal particles relative to the total weight of metal particles plus polymer binder. As shown in FIG. 19, the average pore size for the pores in the pore network of the porous metal structure does not appear to change substantially based on sintering temperature and/or based on the relative amounts of metal and binder. However, increasing the sintering temperature when forming the porous metal structure does appear to reduce the overall volume of available pores, based on the reduced peak intensity with increasing temperature. This reduction in available pore volume is believed to correspond to a reduction in the number of available pore channels for permeation.

Figure 20:
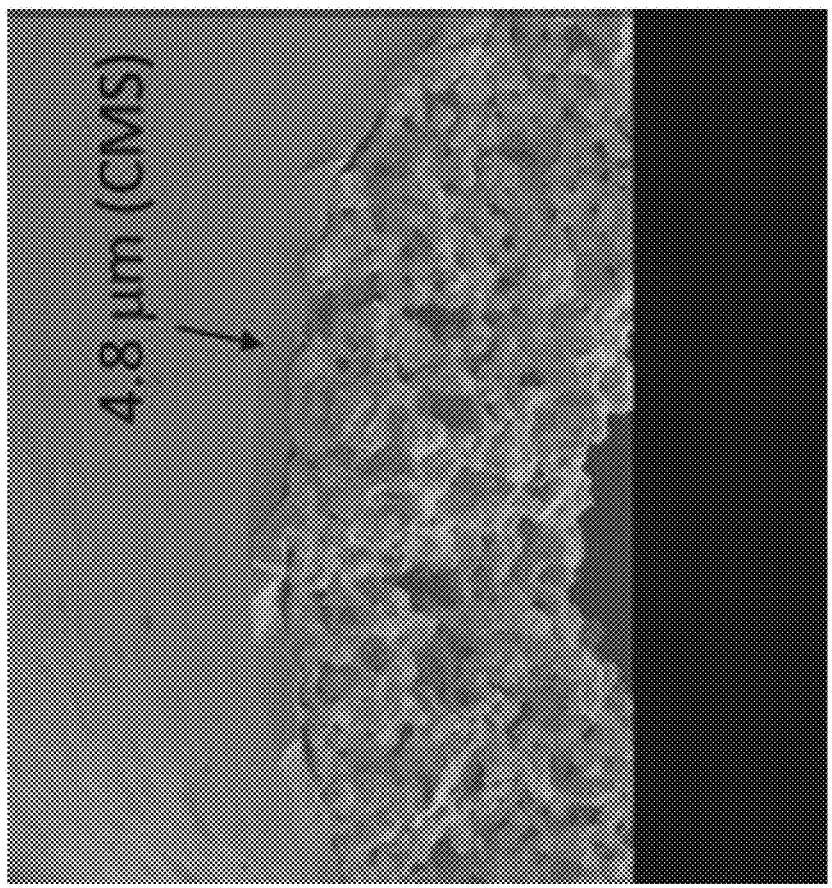
FIG. 20 shows an example of an asymmetric membrane structure.

The porous metal membrane structure was then coated with Matrimid® 5218 to form a coating layer using a dip coating procedure. The porous metal membrane structure was dip coated using a 15 wt % polymer solution balanced with dichloromethane (i.e., 15 wt % polymer in dichloromethane solvent). The resulting coating layer was pyrolyzed at a temperature of about 550° C. for about 120 minutes (after a suitable temperature program to ramp to 550° C.) to form an asymmetric membrane structure as shown in FIG. 20. The pyrolysis method was otherwise similar to pyrolysis of an asymmetric membrane as described herein. After pyrolysis, the selective layer of the asymmetric membrane structure had a smallest median pore size peak of between 3 and 4 Angstroms. A single fiber of the asymmetric membrane structure with an active length of about 7 cm was loaded into a module for characterization of the asymmetric membrane structure. The He/$N_2$ selectivity of the fiber was about 13.8, which is believed to indicate that the asymmetric membrane structure was substantially free of mesopore (or larger) defects.

Figure 21:
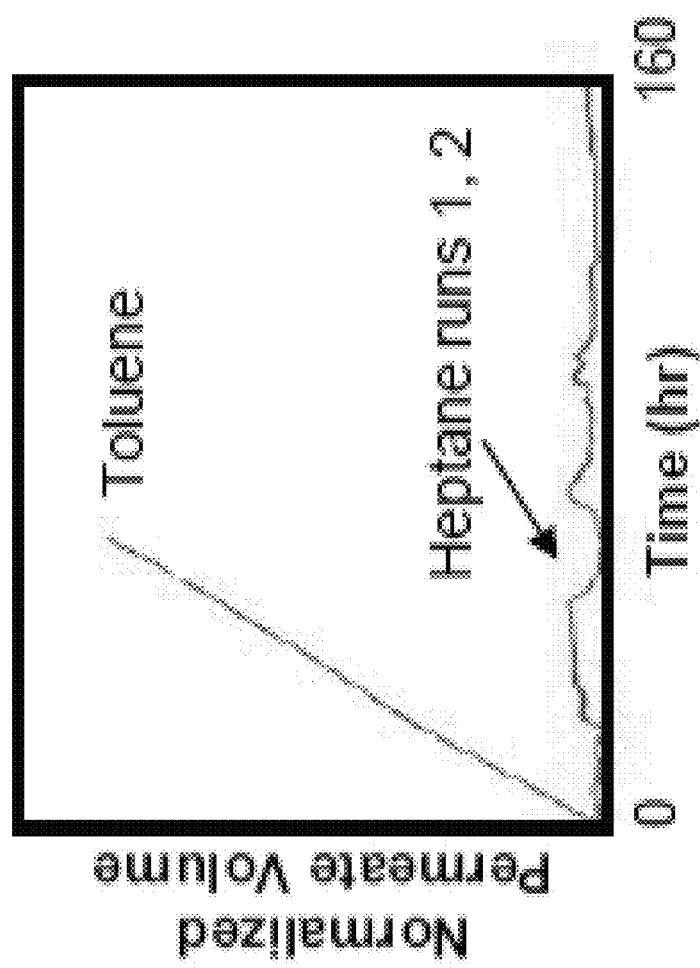
FIG. 21 shows examples of single component permeance through an asymmetric membrane structure for toluene and n-heptane.

The fiber corresponding to the asymmetric membrane structure was also characterized based on single component liquid phase permeation of toluene and n-heptane at 22° C. and a similar pressure for both components. The single component permeation of toluene and n-heptane through the membrane at the reverse osmosis conditions as a function of time is shown in FIG. 21. FIG. 21 shows that toluene was able to pass through the asymmetric membrane structure, while the amount of n-heptane permeance was more limited. For the steady state single component permeance amounts shown in FIG. 21, the single component toluene liquid phase permeance was about $5.09 \times 10^{15}$ mol/$m^2$-s-Pa, while the single component n-heptane liquid phase permeance was about $6.04 \times 10^{-17}$ mol/$m^2$-s-Pa. This corresponds to a selectivity for toluene relative to n-heptane of about 84. This can appear to be a surprising result, as the conventional molecular diameter of toluene is about 5.8 Angstroms while the conventional molecular diameter of n-heptane is about 4.3 Angstroms. However, due to the primarily planar nature of the toluene ring, it may be possible that in some orientations the apparent molecular diameter of toluene can be smaller than n-heptane. Additionally or alternately, the porous carbon membrane may have some similarity in surface properties to an asphaltenic material. It is possible that the relatively low solubility of n-heptane in asphaltenic materials is related to n-heptane having a reduced permeance. Based on the He/$N_2$ selectivity of 13.8 (derived from single component permeance) noted above, it is believed that the porous carbon membrane is relatively free of defects, and therefore it is not believed that the toluene is being primarily transported in mesoporous channels. Based on FIG. 21, for a separation of toluene from n-heptane by reverse osmosis, it is believed that the rate of transport of toluene into the permeate can be enhanced by increasing the pressure for the separation conditions.

ADDITIONAL EMBODIMENTS

Embodiment 1

A system for xylene isomerization and separation, comprising: a separation stage based on boiling point separation configured to generate at least a para-xylene enriched fraction; a xylene recovery unit in fluid communication with the separation stage for receiving the para-xylene enriched fraction from the separation stage, the xylene recovery unit comprising a product outlet and a residual outlet; a membrane structure in fluid communication with the residual outlet for receiving at least a portion of residual stream; and a liquid phase isomerization reactor in fluid communication with the membrane structure for receiving a retentate from the membrane structure, wherein the membrane structure comprises a plurality of membrane layers, a first membrane layer of the membrane structure comprising a porous metal structure or a porous carbon layer having a pore volume of at least 0.2 cm$^3$/g of pores with a median pore size of at least 20 nm, a second membrane layer of the membrane structure comprising a porous carbon layer having a BET surface area of at least about 100 m$^2$/g, the second membrane layer having a pore size distribution comprising a smallest substantial pore size peak having a median pore size of about 5.8 Angstroms to about 7.0 Angstroms, or about 6.0 Angstroms to about 7.0 Angstroms, or about 5.8 Angstroms to about 6.8 Angstroms, or about 6.0 Angstroms to about 6.5 Angstroms.

Embodiment 2

The system of Embodiment 1, wherein the separation stage is further configured to generate a lower boiling fraction, an ortho-xylene enriched fraction, a bottoms fraction, or a combination thereof.

Embodiment 3

The system of Embodiment 1 or 2, wherein the xylene recovery unit comprises a para-xylene crystallizer, a simulated moving bed separator, or a combination thereof.

Embodiment 4

A system for xylene isomerization and separation, comprising: a separation stage based on boiling point separation configured to generate at least a para-xylene enriched fraction; at least one membrane structure for forming a permeate comprising para-xylene and a retentate; and an isomerization reactor in fluid communication with the membrane structure for receiving the retentate from the membrane structure, wherein the at least one membrane structure comprises a plurality of membrane layers, a first membrane layer of the membrane structure comprising a porous metal structure or a porous carbon layer having a pore volume of at least 0.2 cm$^3$/g of pores with a median pore size of at least 20 nm, a second membrane layer of the membrane structure comprising a porous carbon layer having a BET surface area of at least about 100 m$^2$/g, the second membrane layer having a pore size distribution comprising a smallest substantial pore size peak having a median pore size of about 5.8 Angstroms to about 7.0 Angstroms, or about 6.0 Angstroms to about 7.0 Angstroms, or about 5.8 Angstroms to about 6.8 Angstroms, or about 6.0 Angstroms to about 6.5 Angstroms.

Embodiment 5

The system of Embodiment 4, wherein the isomerization reactor comprises a liquid phase isomerization reactor.

Embodiment 6

The system of Embodiment 4 or 5, wherein the at least one membrane structure is in fluid communication with the separation stage for receiving the para-xylene enriched stream, the isomerization reactor being in fluid communication with the separation stage for recycle of at least a portion of an isomerized retentate to the separation stage.

Embodiment 7

The system of any of Embodiments 4-6, wherein the at least one membrane structure comprises a first membrane structure and a second membrane structure, the isomerization reactor being in fluid communication with the separation stage for receiving the para-xylene enriched stream, the first membrane structure being in fluid communication with the isomerization reactor for receiving at least a portion of an isomerized para-xylene enriched stream to form a first permeate and a first retentate, the first membrane structure being in fluid communication with the separation stage for recycle of at least a portion of the first retentate to the separation stage, and the second membrane structure being in fluid communication with the first membrane structure for receiving the first permeate to form a second permeate and a second retentate, the second membrane structure being in fluid communication with the isomerization reactor to recycle at least a portion of the second retentate to the isomerization reactor.

Embodiment 8

The system of any of Embodiments 4-7, the system further comprising a xylene recovery unit, the isomerization reactor being in fluid communication with the separation stage for receiving the para-xylene enriched stream, the at least one membrane structure being in fluid communication with the isomerization reactor for receiving at least a portion of an isomerized para-xylene enriched stream to form a permeate and a retentate, the first membrane structure being in fluid communication with the separation stage for recycle of at least a portion of the retentate to the separation stage, and the xylene recovery unit being in fluid communication with the at least one membrane structure for receiving at least a portion of the permeate, the xylene recovery unit comprising a product outlet and a residual outlet, the isomerization reactor being in fluid communication with the residual outlet.

Embodiment 9

A method for xylene isomerization and separation, comprising: exposing a xylene-containing feed to an isomerization catalyst under liquid phase isomerization conditions to produce an isomerized effluent; and performing a membrane separation using a membrane structure on at least a portion of the xylene-containing feed, at least a portion of the isomerized effluent, or a combination thereof to produce a permeate enriched in para-xylene relative to the xylene-containing feed and/or the isomerized effluent, wherein the membrane structure comprises a plurality of membrane layers, a first membrane layer of the membrane structure comprising a porous metal structure or a porous carbon layer having a pore volume of at least 0.2 cm$^3$/g of pores with a median pore size of at least 20 nm, a second membrane layer of the membrane structure comprising a porous carbon layer having a BET surface area of at least about 100 m$^2$/g, the second membrane layer having a pore size distribution comprising a smallest substantial pore size peak having a median pore size of about 5.8 Angstroms to about 7.0 Angstroms, or about 6.0 Angstroms to about 7.0 Angstroms, or about 5.8 Angstroms to about 6.8 Angstroms, or about 6.0 Angstroms to about 6.5 Angstroms.

Embodiment 10

The method of Embodiment 9, further comprising separating a feedstock to form at least a first fraction and a lower boiling fraction, at least a first fraction and a higher boiling fraction, or a combination thereof, the xylene-containing feed comprising at least a portion of the first fraction.

Embodiment 11

The method of any of Embodiments 9-10, wherein performing a membrane separation further comprises forming a retentate, the xylene-containing feed comprising at least a portion of the retentate.

Embodiment 12

The method of any of Embodiments 9-11, further comprising recovering xylene from the permeate using a para-xylene crystallizer, a simulated moving bed separator, or a combination thereof.

Embodiment 13

The method of any of Embodiments 9-12, wherein the membrane separation is performed at a temperature of about 180° C. to about 300° C., or about 200° C. to about 280° C.

Embodiment 14

The method of any of Embodiments 9-13, wherein performing the membrane separation comprises using a plurality of the membrane structure, the at least a portion of the xylene-containing feed being exposed to a first membrane structure to form a first permeate, at least a portion of the first permeate being exposed to a second membrane structure to form a second permeate.

Embodiment 15

The system or method of any of Embodiments 1-14, wherein the membrane structure comprises a storage modulus of at least about 200 MPa at 100° C.

Embodiment 16

The system or method of any of Embodiments 1-15, wherein the smallest substantial pore size peak has a peak width at half of the peak height of about 1.0 Angstrom or less.

Embodiment 17

A permeate comprising para-xylene formed according to the system or method of any of the above embodiments.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A system for xylene isomerization and separation, comprising:
   a separation stage based on boiling point separation configured to generate at least a para-xylene enriched fraction;
   a xylene recovery unit in fluid communication with the separation stage for receiving the para-xylene enriched fraction from the separation stage, the xylene recovery unit comprising a product outlet and a residual outlet;
   a membrane structure in fluid communication with the residual outlet for receiving at least a portion of residual stream; and
   a liquid phase isomerization reactor in fluid communication with the membrane structure for receiving a retentate from the membrane structure,
   wherein the membrane structure comprises a plurality of membrane layers, a first membrane layer of the membrane structure comprising a pore volume of at least 0.2 cm$^3$/g of pores with a median pore size of at least 20 nm, a second membrane layer of the membrane structure comprising a porous carbon layer having a BET surface area of at least about 100 m$^2$/g, the second membrane layer having a pore size distribution comprising a smallest substantial pore size peak having a median pore size of about 5.8 Angstroms to about 6.8 Angstroms.

2. The system of claim 1, wherein the separation stage is further configured to generate a lower boiling fraction, a bottoms fraction, or a combination thereof.

3. The system of claim 1, wherein the xylene recovery unit comprises a para-xylene crystallizer, a simulated moving bed separator, or a combination thereof.

4. The system of claim 1, wherein the first membrane layer comprises a porous carbon layer or wherein the first membrane layer comprises a porous metal structure.

5. A system for xylene isomerization and separation, comprising:
   a separation stage based on boiling point separation configured to generate at least a para-xylene enriched fraction;
   at least one membrane structure for forming a permeate comprising para-xylene and a retentate; and
   an isomerization reactor in fluid communication with the membrane structure for receiving the retentate from the membrane structure,
   wherein the at least one membrane structure comprises a plurality of membrane layers, a first membrane layer of the membrane structure comprising a pore volume of at least 0.2 cm$^3$/g of pores with a median pore size of at least 20 nm, a second membrane layer of the membrane structure comprising a porous carbon layer having a BET surface area of at least about 100 m$^2$/g, the second membrane layer having a pore size distribution comprising a smallest substantial pore size peak having a median pore size of about 5.8 Angstroms to about 6.8 Angstroms.

6. The system of claim 5, wherein the isomerization reactor comprises a liquid phase isomerization reactor.

7. The system of claim 5, wherein the at least one membrane structure is in fluid communication with the separation stage for receiving the para-xylene enriched stream, the isomerization reactor being in fluid communication with the separation stage for recycle of at least a portion of an isomerized retentate to the separation stage.

8. The system of claim 5, wherein the at least one membrane structure comprises a first membrane structure and a second membrane structure,
the isomerization reactor being in fluid communication with the separation stage for receiving the para-xylene enriched stream,
the first membrane structure being in fluid communication with the isomerization reactor for receiving at least a portion of an isomerized para-xylene enriched stream to form a first permeate and a first retentate, the first membrane structure being in fluid communication with the separation stage for recycle of at least a portion of the first retentate to the separation stage, and
the second membrane structure being in fluid communication with the first membrane structure for receiving the first permeate to form a second permeate and a second retentate, the second membrane structure being in fluid communication with the isomerization reactor to recycle at least a portion of the second retentate to the isomerization reactor.

9. The system of claim 5, the system further comprising a xylene recovery unit, the isomerization reactor being in fluid communication with the separation stage for receiving the para-xylene enriched stream,
the at least one membrane structure being in fluid communication with the isomerization reactor for receiving at least a portion of an isomerized para-xylene enriched stream to form a permeate and a retentate, the at least one membrane structure being in fluid communication with the separation stage for recycle of at least a portion of the retentate to the separation stage, and
the xylene recovery unit being in fluid communication with the at least one membrane structure for receiving at least a portion of the permeate, the xylene recovery unit comprising a product outlet and a residual outlet, the isomerization reactor being in fluid communication with the residual outlet.

10. The system of claim 5, wherein the first membrane layer comprises a porous carbon layer or wherein the first membrane layer comprises a porous metal structure.

* * * * *